US009314926B2

(12) United States Patent
Bailey et al.

(10) Patent No.: US 9,314,926 B2
(45) Date of Patent: Apr. 19, 2016

(54) COMPACT NEEDLE MANIPULATOR FOR TARGETED INTERVENTIONS

(71) Applicant: INTUITIVE SURGICAL OPERATIONS, INC., Sunnyvale, CA (US)

(72) Inventors: David W. Bailey, Portola Valley, CA (US); Simon P. DiMaio, Sunnyvale, CA (US); Tao Zhao, Sunnyvale, CA (US); Lawton N. Verner, Santa Clara, CA (US); Alan E. Loh, Los Altos, CA (US); Jonathan Sorger, Belmont, CA (US); Bruce Michael Schena, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 556 days.

(21) Appl. No.: 13/767,856

(22) Filed: Feb. 14, 2013

(65) Prior Publication Data

US 2013/0209208 A1 Aug. 15, 2013

Related U.S. Application Data

(60) Provisional application No. 61/599,339, filed on Feb. 15, 2012.

(51) Int. Cl.
*A61B 19/00* (2006.01)
*B25J 11/00* (2006.01)
*B25J 5/02* (2006.01)

(Continued)

(52) U.S. Cl.
CPC .............. *B25J 11/00* (2013.01); *A61B 19/2203* (2013.01); *B25J 5/02* (2013.01); *B25J 9/1065* (2013.01); *A61B 19/201* (2013.01); *A61B 2017/00274* (2013.01); *A61B 2017/3409* (2013.01); *A61B 2018/1425* (2013.01); *A61B 2019/265* (2013.01); *A61B 2019/5259* (2013.01); *A61B 2019/5454* (2013.01); *A61B 2019/5483* (2013.01)

(58) Field of Classification Search
CPC .................... A61B 19/2203; A61B 2019/5259
USPC ............................................. 606/1
See application file for complete search history.

(56) References Cited

U.S. PATENT DOCUMENTS 6,665,554 B1 * 12/2003 Charles ................ A61B 19/201
600/427
6,723,106 B1 * 4/2004 Charles .............. A61B 19/2203
606/130

(Continued)

OTHER PUBLICATIONS

U.S. Appl. No. 13/767,801, filed Feb. 14, 2013, Bailey.

*Primary Examiner* — Gary Jackson
*Assistant Examiner* — Amanda Steinberg

(57) ABSTRACT

Embodiments of an instrument manipulator are disclosed. An instrument manipulator can include a track; a translational carriage coupled to ride along the track; a shoulder yaw joint coupled to the translational carriage; a shoulder pitch joint coupled to the shoulder yaw joint, the shoulder pith joint including an arm, a wrist mount coupled to the arm, struts coupled between the wrist mount and the shoulder yaw joint, and a shoulder pitch mechanism coupled to the arm; a yaw-pitch-roll wrist coupled to the wrist mount, the yaw-pitch-roll wrist including a yaw joint and a differentially driven pitch-roll joint; and an instrument mount coupled to the wrist. The various joints and carriages can be driven by motors.

24 Claims, 23 Drawing Sheets

(51) Int. Cl.
*B25J 9/10* (2006.01)
*A61B 17/00* (2006.01)
*A61B 18/14* (2006.01)
*A61B 17/34* (2006.01)

(56) References Cited

U.S. PATENT DOCUMENTS

| | | | | |
|---|---|---|---|---|
| 2006/0045672 | A1* | 3/2006 | Maynard | B25J 5/02 414/276 |
| 2008/0314181 | A1* | 12/2008 | Schena | A61B 19/22 74/469 |
| 2009/0024141 | A1* | 1/2009 | Stahler | A61B 19/2203 606/130 |
| 2009/0247859 | A1* | 10/2009 | Daum | A61B 19/20 600/411 |
| 2009/0326365 | A1* | 12/2009 | Goldenberg | A61B 19/2203 600/411 |
| 2010/0056900 | A1* | 3/2010 | Whitcomb | A61B 5/055 600/414 |
| 2010/0198052 | A1* | 8/2010 | Jenkins | A61B 5/0555 600/417 |
| 2011/0071380 | A1* | 3/2011 | Goldenberg | A61B 5/055 600/411 |
| 2011/0238083 | A1* | 9/2011 | Moll | A61B 17/062 606/130 |

* cited by examiner

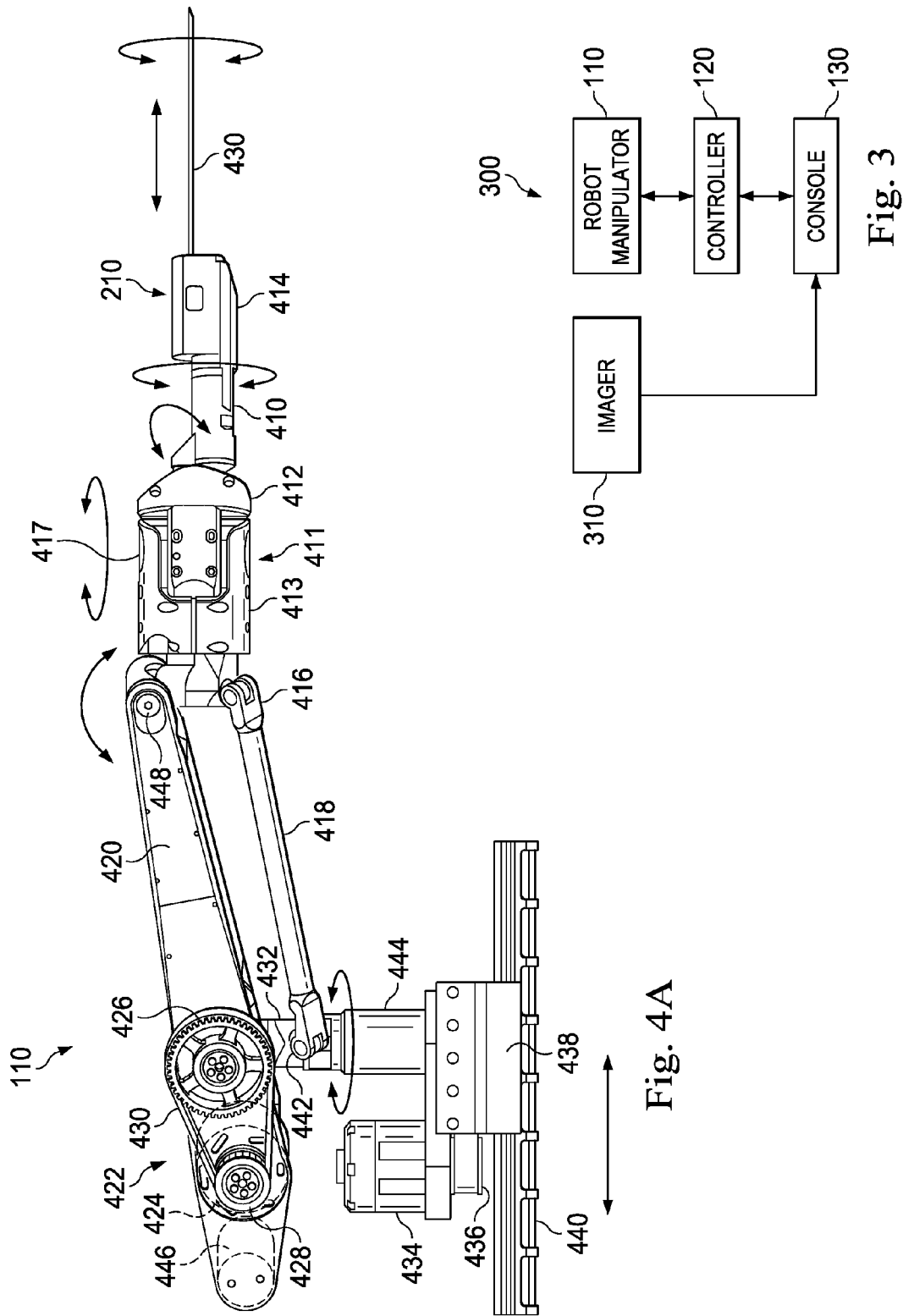

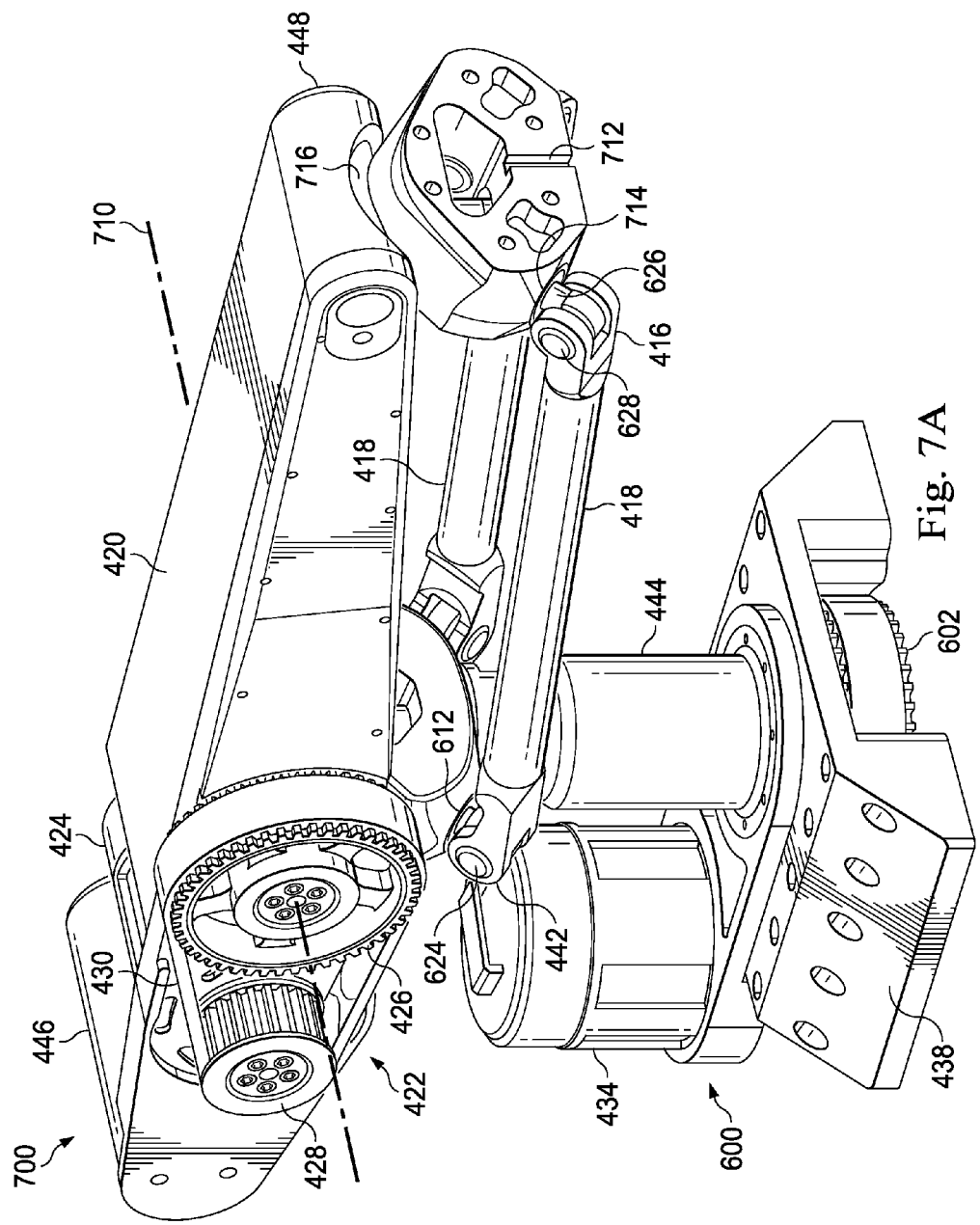

COMPACT NEEDLE MANIPULATOR FOR TARGETED INTERVENTIONS

RELATED APPLICATIONS

This application claims priority to U.S. Provisional Patent Application Ser. No. 61/599,339, filed on Feb. 15, 2012, which is herein incorporated by reference in its entirety.

TECHNICAL FIELD

Embodiments of the present invention are related to a robotic manipulator that delivers a needle through the perineum.

DISCUSSION OF RELATED ART

Each year 1.5 million core needle biopsies are performed, yielding several hundred thousand new cases of prostate cancer. In many cases, early detection of the cancer results in higher efficacy of the treatment methods utilized.

Further, MRI-guided needle based therapies (biopsies, localized laser ablations, delivery of implantable seeds utilized in low-dose-rate (LDR) permanent brachytherapy, which is a common treatment for prostrate cancer, or other treatment) have been demonstrated to be successful. However, manipulation of the needle in the confined space afforded by the typical MRI instrument has proven challenging.

Some have provided solutions with robots powered by air, ultrasonics, or piezoelectrics. However, these methods do not provide the dexterity and power that is sought in such an environment.

Prostate cancer is among the most common noncutaneous cancers in American men. There are two common screening methods for prostate cancer, namely the prostate-specific antigen test (PSA) and the digital rectal exam (DRE). The PSA test, which determines a likelihood of prostate cancer from antigen concentrations in the blood sample, is not conclusive. In the DRE, the physician can determine whether the prostate gland is enlarged or there are abnormal nodules present. In either case, needle biopsies are often recommended to determine if tumors exist and whether or not any tumor is benign or malignant.

A current standard of care for investigating the existence of a tumor is by transrectal ultrasound (TRUS). Under ultrasound guidance, the physician can place a biopsy needle through the wall of the rectum into the prostate gland. The biopsy needle removes a small cylinder of tissue for further testing. Usually, multiple samples are removed for testing during the procedure. The TRUS procedure has proven not to be very accurate for tumor localization. Other forms of imaging such as Magnetic Resonance Imaging (MRI) and computed tomography (CT) X-Ray imaging are capable of high spatial resolution and enables better identification of individual tumors.

There have been various attempts to combine robotic needle manipulators with various imaging techniques in order to more accurately perform needle based treatments, including biopsies. However, there remains a need to develop better performing manipulators for needle based procedures performed within an imaging environment.

SUMMARY

In accordance with aspects of the present invention, embodiments of an instrument manipulator are disclosed. In some embodiments, an instrument manipulator can include a track; a translational carriage coupled to ride along the track, the translational carriage being propelled along the track by a linear motor; a shoulder yaw joint coupled to the translational carriage, the shoulder yaw joint being actuated by a shoulder yaw motor; a shoulder pitch joint coupled to the shoulder yaw joint, the shoulder pitch joint including an arm, a wrist mount coupled to the arm, struts coupled between the wrist mount and the shoulder yaw joint and forming a 3D parallelogram, and a shoulder pitch motor coupled to actuate the shoulder pitch joint, the struts, the arm, and the wrist mount; a yaw-pitch-roll wrist coupled to the wrist mount, the yaw-pitch-roll wrist including a yaw joint actuated by one or more wrist yaw motors and a differentially driven pitch-roll joint actuated by differentially driven pitch-roll motors; and an instrument mount coupled to the wrist, the instrument mount having one or more instrument motors providing an instrument drive.

These and other embodiments are further discussed below with respect to the following figures.

BRIEF DESCRIPTION OF THE DRAWINGS

FIG. 3 illustrates a block diagram of a manipulator system according to some embodiments of the present invention.

FIG. 4A illustrates a robot manipulator according to some embodiments of the present invention.

FIG. 7A illustrates shoulder pitch joint of the robot manipulator illustrated in FIG. 4A.

DETAILED DESCRIPTION

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Further, this description's terminology is not intended to limit the invention. For example, spatially relative terms—such as "beneath", "below", "lower", "above", "upper", "proximal", "distal", "horizontal", "vertical" and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

There are clinical trends towards focal/targeted therapies of pathologies in situ. These therapies, if effective, may offer significant reduction in invasiveness as compared to more traditional extirpative surgery. Robotic based technologies may help to address clinical needs in this area. Throughout this disclosure, treatment of prostate cancer is utilized as an example of such a focal therapy. That is not to be interpreted as the only utilization for embodiments that are disclosed here.

Figure 1:
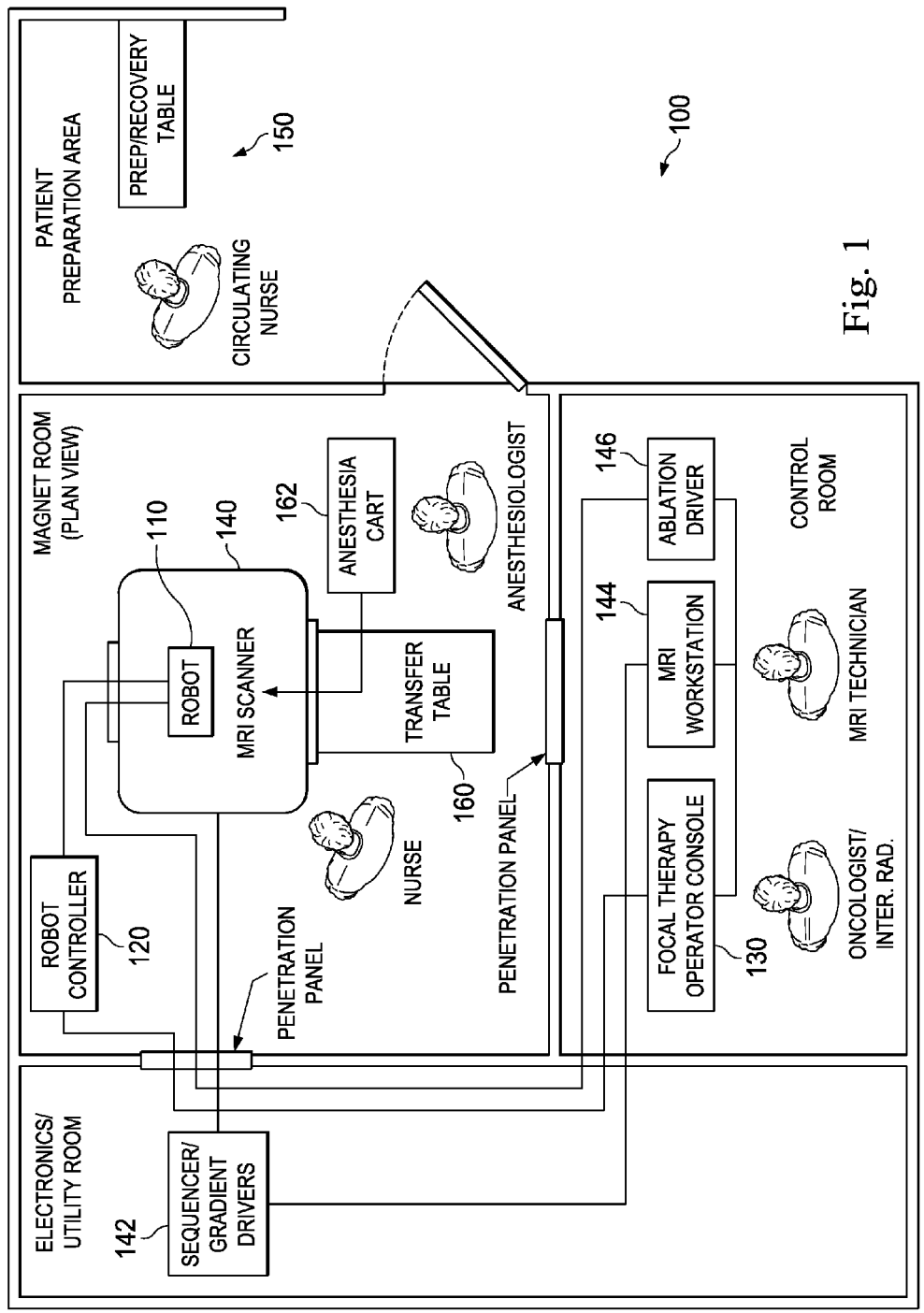
FIG. 1 illustrates a surgical environment in which a manipulator according to some embodiments of the present invention can be utilized.

FIG. 1 illustrates a system 100 that can utilize a robot system according to some embodiments of the present invention. As shown in FIG. 1, robot manipulator 110 can be located within scanner 140. Although scanner 140 is depicted as an MRI scanner in this example, scanner 140 can be any other type of scanner as well (e.g., CT, ultrasound, X-Ray, PET, etc.). The movement of robot 110 is controlled by a robot controller 120. Robot controller 120 communicates with an operator console 130 and translates instructions from operator console 130 into coordinated motions of the various motorized joints in robot 110.

Scanner 140 is coupled to a scanner controller 142. Scanner controller 142 communicates with a workstation 144. Workstation 144, in communication with scanner controller 142, operates scanner 140 to produce images.

A patient is positioned on a transfer table 160 along with robot 110 and placed inside scanner 140, or positioned relative to scanner 140 in such a manner as to allow robot 110 to access the surgical area and allow scanner 140 to provide images of the same surgical area. The image of the surgical area is input to the operator console 130, which registers the position of robot 110 to the image received from scanner 140. In that fashion, an operator at operator console 130 can direct robot 110 to act on specifically identified targets in the surgical area by placing a needle at or near that target.

In some cases, a separate driver 146 for different modalities of treatment, for example laser ablation, can be utilized. Further, the system can include an anesthesia cart 162 to be used in keeping the patient sedated and a patient preparation or recovery area 150.

Figure 2:
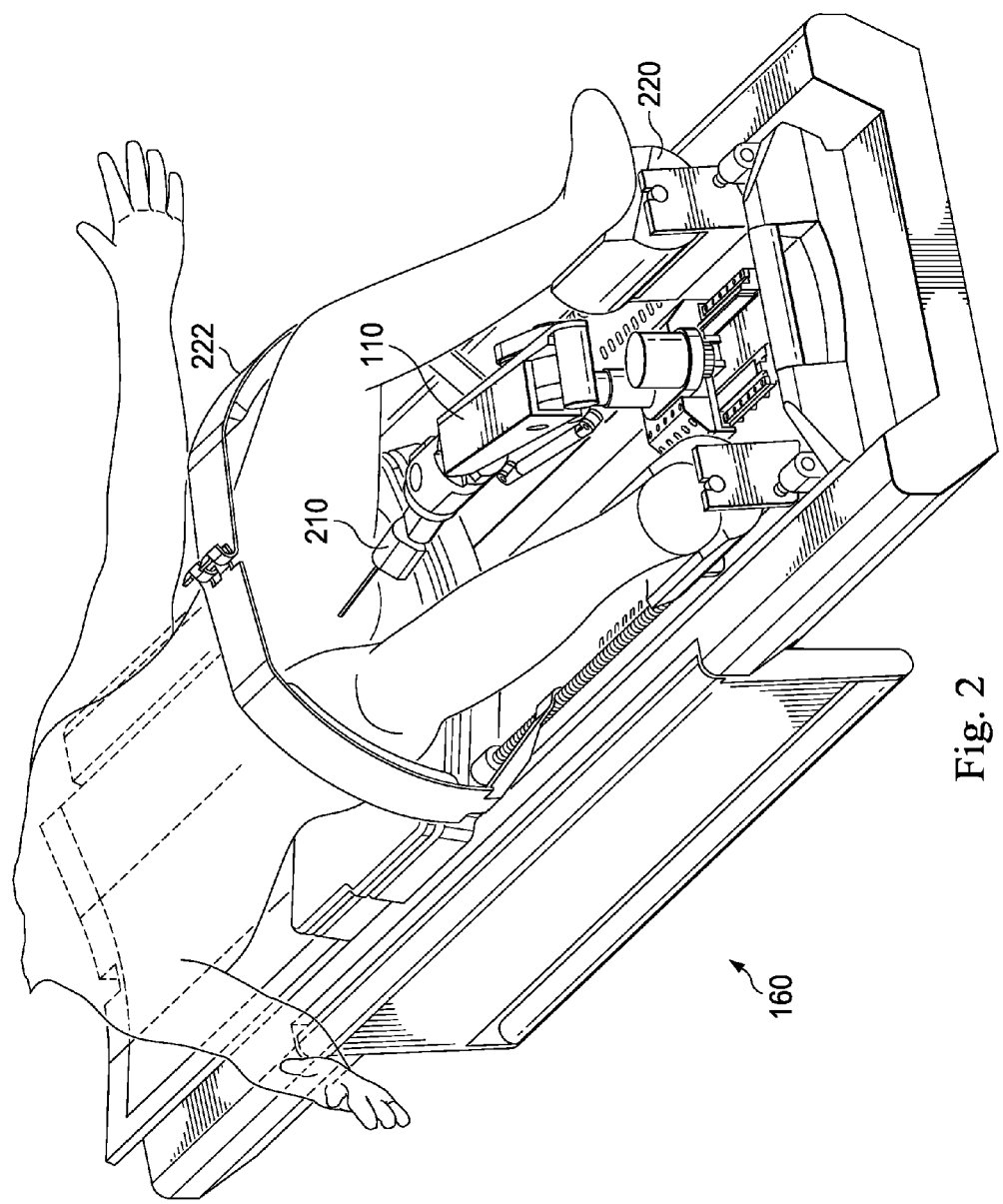
FIG. 2 illustrates a robot manipulator according to some embodiments of the present invention mounted on a scanner transfer table.

FIG. 2 illustrates table 160 with robot manipulator 110 mounted thereon. Robot 110 operates as a needle manipulator and, as shown in FIG. 2, a needle based instrument 210 is coupled to robot 110. Table 160 may also include foot rests 220 and patient mounts 222 that can be utilized to hold the patient relatively fixed with respect to robot 110 during the procedure. As shown in FIG. 2, robot manipulator 110 is mounted to table 160 and is capable of linear motion along the length of table 160. Robot 110 is compact enough to reside between the legs of the patient on table 160 and to operate within the confined space of, for example, an MRI instrument bore. Further, robot 110 is constructed of materials that are not substantially affected by, and do not substantially affect, any magnetic fields produced by the imager in an imaging field of interest.

FIG. 3 illustrates a block diagram of robot system 300 according to some embodiments of the present invention. As shown in FIG. 3, robot manipulator 110 (also referred to herein as a robot or a manipulator) is controlled by controller 120. Controller 120 interacts with console 130. Imager 310 also interacts with user console 130. Console 130 receives input from both controller 120 and imager 310 in order to register robot 110 with the images provided by imager 310. Imager 310 can be an MRI imager, as is illustrated in FIG. 1, but may also be other imaging modalities, for example a CT X-Ray imager. Registration of robot 110 with imager 310 allows an operator at console 130 to direct controller 120 to place a needle 430 of needle based instrument 210 at a particular location in the patient as directed by the operator informed by the image. Controller 120 then provides electrical inputs to control the motion at various joints in robot 110 to fulfill those instructions.

FIG. 4A illustrates an embodiment of robot manipulator 110. Robot 110 is shown with needle based instrument 210, with needle 430, attached to an instrument mount 410. Needle based instrument 210 can be mounted to mount 410 through a sterile adaptor 414. Needle based instrument 210 and sterile adaptor 414 can be easily removed from robot 110. Needle based instrument 210 can take inputs from robot 110 through mount 410. For example, needle 430 can be rotated, needle 430 can be extended, and inserts to needle 430 can be manipulated through the inputs on mount 410.

Needle based instrument 210, with needle 430, can be a biopsy instrument, can facilitate optical fiber or RF antennas for optical or RF based laser ablation techniques, can provide the delivery of implantable seeds for an LDR treatment, can provide for the delivery of other substances involved in the treatment, or provide other needle based treatments. Instrument 210 can be a single use or disposable instrument that is utilized in only one operation. As such, a sterile adaptor 414 can be provided between instrument 210 and mount 410. Instrument inputs provided to mount 410 can be coupled to instrument 210 through the sterile adaptor between instrument 210 and mount 410. During the treatment, robot 110 can be draped so that the area of instrument 210 remains a sterile environment. Examples of needle based instrument 210 are further discussed in co-filed U.S. Provisional Application No. 61/599,300, which is herein incorporated by reference in its entirety.

Control inputs to mount 410 are provided by one or more instrument motors in mount 410, which provide input drives to instrument 210, in some embodiments through a sterile adapter 414. In some embodiments, there may be any number of motors in mount 410. In some examples, there are two to provide two degrees of freedom (DoFs) within instrument 210. Instrument 210 can provide several DoFs to needle 430. For example, instrument 210 may provide a roll or a translational motion, powered by the input drives from mount 410. In laser or RF ablation treatment, for example, instrument 210 may retract needle 430 and push forward an optical fiber or an RF antenna once needle 430 is positioned appropriately for treatment. Further, mechanisms in instrument 210 may allow for the insertion of substances, the deposition of seeds, or other deliveries for particular treatments.

Instrument 210 may include a processor and memory that is interfaced to controller 120 through mount 410. Instrument 210 may, upon startup or insertion of instrument 210 onto mount 410, transmit information such as instrument type, instrument serial number, instrument operational characteristics, and instrument usage history to controller 120. Instrument 210 may also include fiducials mounted along instrument 210 that can be used for determining the location of needle 430 within an image.

Mount 410 is coupled to a yaw-pitch-roll wrist 411, which has a yaw, pitch, and roll DoFs. Wrist 411 includes section 413 and section 412. Section 412 is mechanically coupled to section 413 at yaw joint 417. Roll and pitch DoFs are implemented by a pair of wrist pitch-roll motors housed in section 412 operating in a differential fashion, as is discussed further below. Section 412 is rotated about yaw axis 417 by one or more wrist yaw motors mounted in section 413, as is discussed further below.

Wrist 411 is mounted to an arm 420 at joint 448 and to struts 418 at joint 416. Arm 420 is mounted on a shaft 432. Struts 418 are coupled to a support housing 444, through which shaft 432 passes, at pivot joint 442. Arm 420 and struts 418 establish a 3-D parallelogram structure for support of wrist 411. Arm 420 can be raised and lowered by a shoulder pitch drive mechanism 422. As discussed further below, the shoulder pitch joint can be formed by a cross support (see cross support 702 in FIG. 7B) that passes through arm 420 and is attached to pulley gear 426, around which arm 420 rotates. Arm 420 and struts 418 are arranged such that section 413 of wrist 411 remain substantially horizontally oriented as arm 420 is raised and lowered. Further, section 413 remains substantially oriented along an insertion axis (the axis along a track 440) as arm 420 is rotated in the horizontal plane. Further, needle 430 is centered such that an axis along needle 430 passes through a center portion of section 412 of wrist 411. The actuation torques utilized to operate wrist 411 may be substantially reduced because the needle insertion force, which may be high, utilized in inserting needle 430 is centered on wrist 411. Further, the 3-D parallelogram formed of Arm 420 and struts 418 also help to reduce the actuation torques on wrist 411. The 3-D parallelogram formed with arm 420 and struts 418 also help to reduce the actuation torques needed to raise and lower arm 420 (also referred to as actuation of the shoulder pitch joint).

Mechanism 422 includes two pulley gears, gears 428 and 426, coupled with a belt 430. Gear 428 is driven by a shoulder pitch motor 424. Arm 420 is counterbalanced by a weight 446 to arrange for offset of the torque of arm 420, wrist 411, mount 410, and needle instrument 210 at a support 432. Pulley gear 426 is fixed on a cross support (see cross support 702 of FIG. 7B) around which arm 420 rotates so that rotation of pulley gear 428 by motor 424 causes arm 420 to raise and lower.

Shaft 432 provides support for arm 420 and passes through housing 444 and into a base 438. Arm 420 is rotated along a horizontal axis on top of shaft 432. Shaft 432 itself can be rotated and is driven by shoulder yaw motor 434. Motor 434 is mechanically coupled to support 432 by a belt 436 coupled to a pulley (not shown in FIG. 4A) that is mounted below shaft 432 in base 438. Together, shaft 432 and arm 420 form a shoulder with a yaw axis around shaft 432 and a horizontally oriented pitch axis that allows for elevation control of section 413 of wrist 411.

Base 438 is connected to a translation carriage (not shown in FIG. 4A), which houses a linear motor (not shown in FIG. 4A) that drives robot 110 along a track 440. The motion of robot 110 along track 440 is referred to as motion along the insertion axis.

Motors 434 and 424 are high power compact motors as described in U.S. Utility application Ser. No. 13/767,801, which is herein incorporated by reference in its entirety. Robot 110 is a compact manipulator that allows for extensive movement of needle 430. As shown in FIG. 2, robot 110 is designed to operate between the legs of a patient and within an imaging instrument, for example an MRI imager. Therefore, all components of robot 110 are non-ferromagnetic. Further, robot 110 allows for operation substantially free of interference from the patient.

As illustrated in FIG. 4A, robot manipulator 110 provides for linear motion along track 440, which as shown in FIG. 2 is positioned to translate generally along the bore of an MRI instrument. The linear motion, therefore, is along the insertion axis directed along track 440. Robot manipulator 110 also provides for horizontal rotation of arm 420 about shaft 432 (rotation in a plane parallel with that of table 160 shown in FIG. 2), which is also referred to as shoulder yaw. Vertical motion of section 413 can be implemented by drive mechanism 422, also referred to as shoulder pitch. During this motion, section 413 remains substantially horizontally oriented through the 3-D parallelogram formed by arm 420 and struts 418. Wrist 411 provides for a yaw axis of rotation about pivot 417. Further, wrist roll and pitch can be provided to mount 410 through section 412 of wrist 411. Further, driven by mount 410, needle instrument 210 can provide further DoFs to needle 430, for example a linear insertion motion and a rotation motion, depending on needle instrument 210.

Figure 4B:
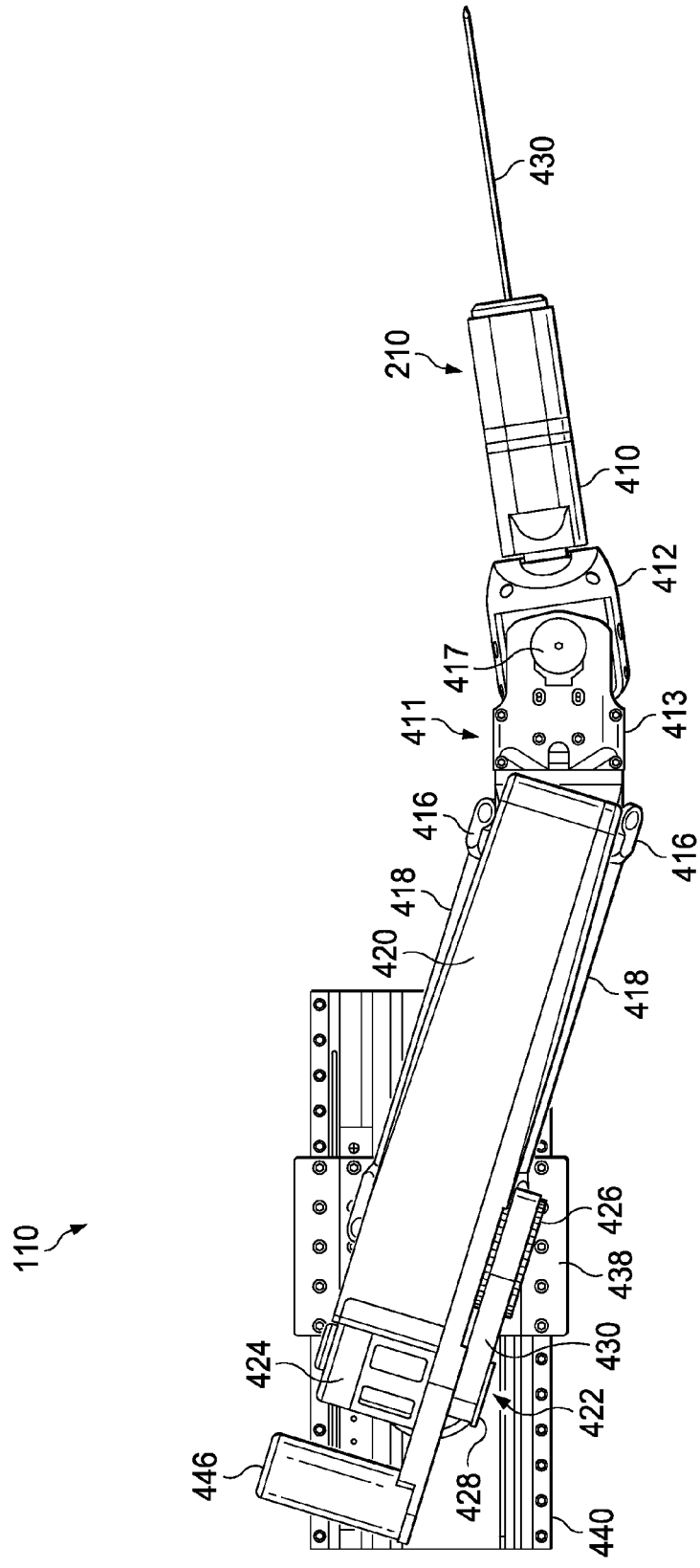
FIGS. 4B and 4C illustrate plan views of the robot manipulator illustrated in FIG. 4A.
Figure 4C:
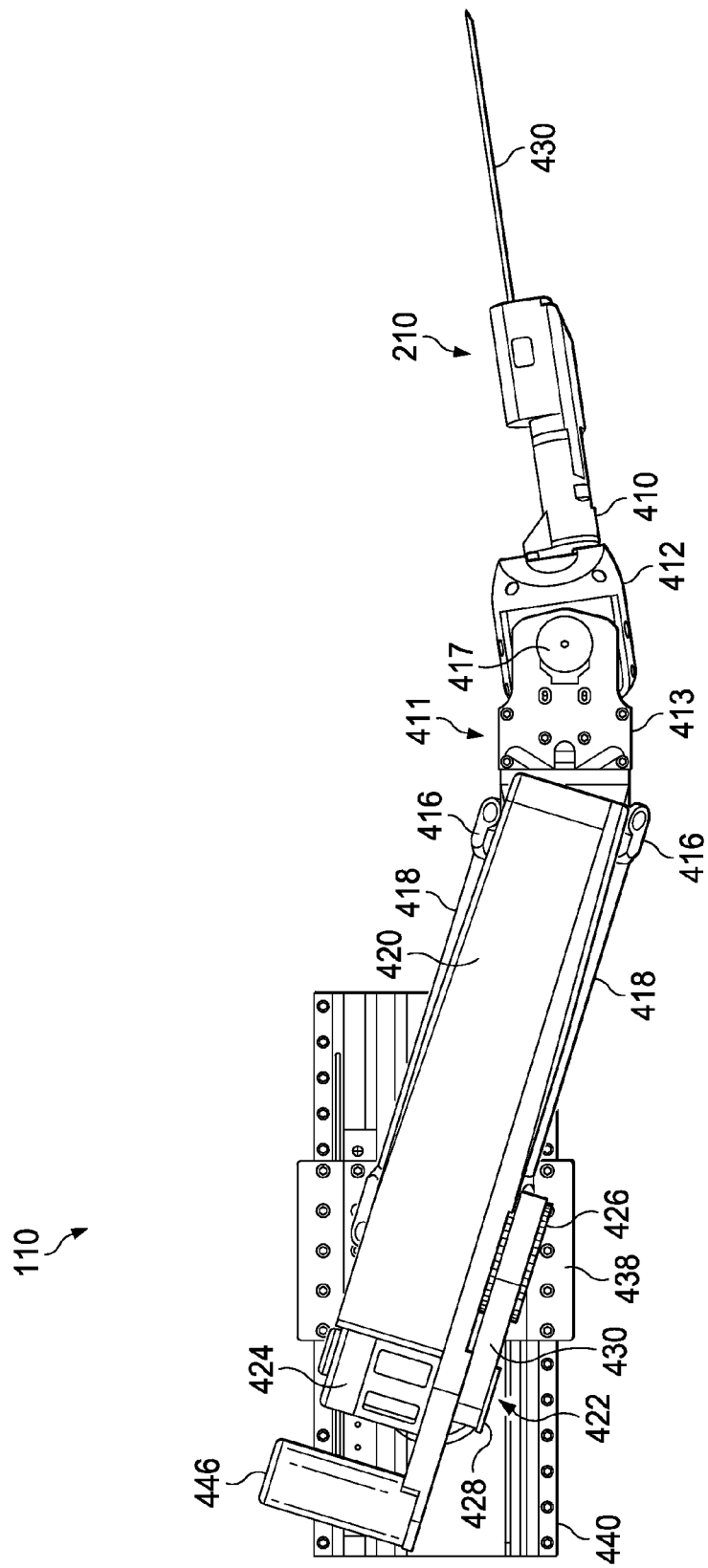

FIG. 4A illustrates robot manipulator 110 with arm 420 raised. FIG. 4B illustrates a plan view of robot 110 with arm 420 rotated about shaft 432 and with a slight yaw on wrist 411. Further, section 413 of wrist 411 remains substantially aligned with track 440. FIG. 4C illustrates another plan view of robot 110 similar to that shown in FIG. 4B, but with mount 410 rotated with section 412 of wrist 411.

As described above, robot manipulator 110 can deliver needle 430 of needle based instrument 210 through the perineum while both the patient and robot manipulator 110 are within the confines of an imager, for example an MRI bore. Control of robot 110 is performed by controller 120 under the direction of console 130, which is controlled by an operator.

Robot 110, under the direction of controller 120, can control the full Cartesian position and rotational orientation of needle based instrument 210. Additionally, control inputs can be provided to needle based instrument 210 through robot 110. As illustrated in FIG. 4A, and discussed above, kinematics of robot 110 includes a linear motion along track 440 driven by a linear motor. Track 440 is generally oriented along the bore of an MRI imager or other imager. Further, shaft 432 can provide a horizontal rotation around support 432 to needle 430. Rotating mount 410 can provide additional clearance against interaction with the patient while keeping needle 430 aligned with section 412 of wrist 411.

Figure 5A:
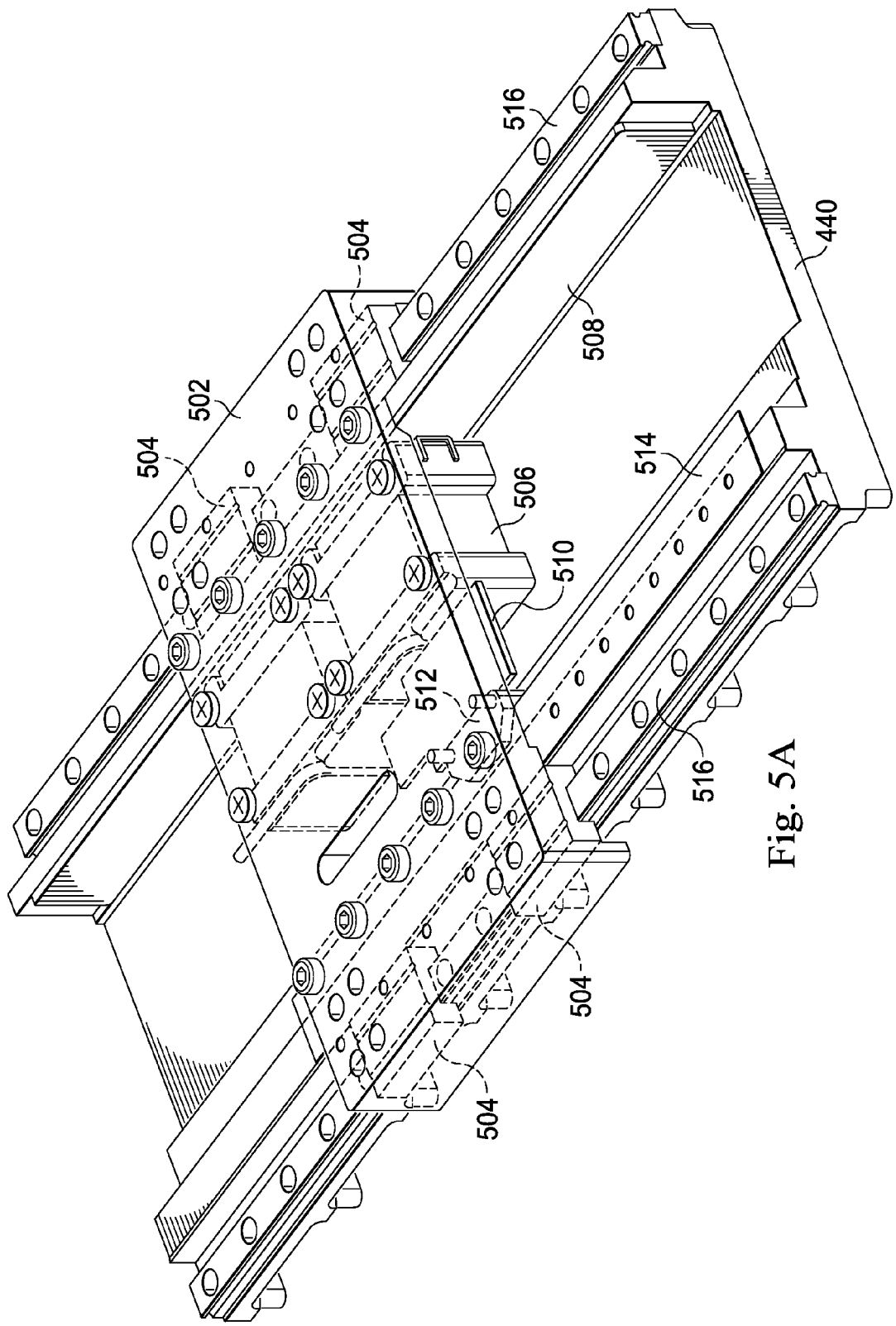
FIGS. 5A and 5B illustrate linear motion along an insertion axis of the robot manipulator illustrated in FIG. 4A.
Figure 5B:
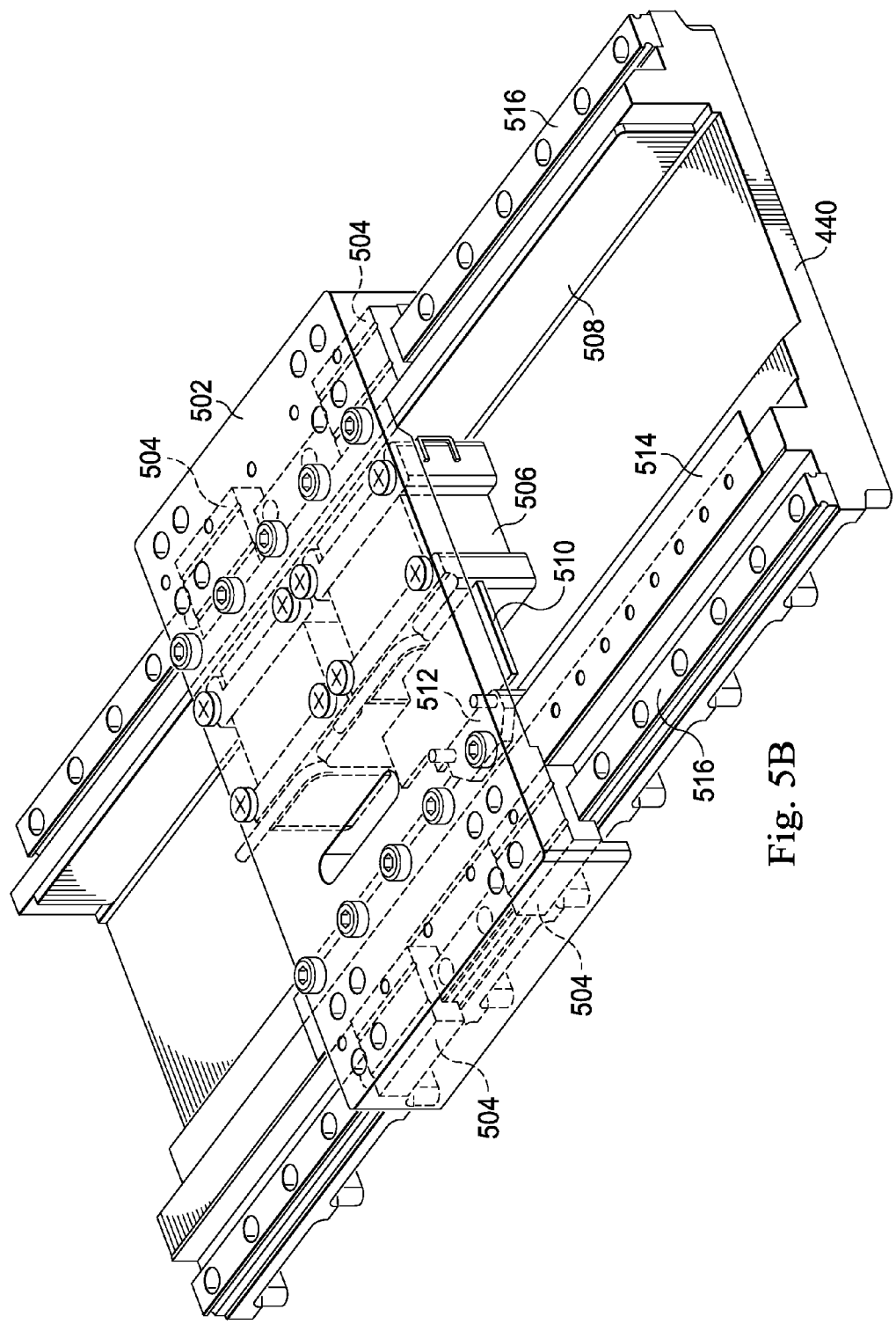

FIGS. 5A and 5B illustrate motion of robot 110 along track 440. As shown in FIGS. 5A and 5B, a translational carriage 502 rides on track 440. Track 440 includes rails 516. Translational carriage 502 includes bearings 504 mechanically attached to carriage 502 that ride on rails 516. As such, carriage 502 can translate along track 440 with bearings 504 riding along rails 516.

As shown in FIGS. 5A and 5B, one or more linear motors 506 are mechanically attached to translational carriage 502 and provide translational forces to translational carriage 502 against a ceramic pad 508. Linear motors 506 can, for example, be piezoelectric motors. Ceramic pad 508 is mechanically attached to track 440 so that the piezoelectric elements of motors 506 engage pad 508 and move translational carriage 502 along track 440. Further, track 440 can be fixed to table 160 shown in FIG. 2 such that the linear motion along track 440, the insertion motion, is directed along the long axis of table 160.

As is further illustrated in FIGS. 5A and 5B, a carriage locator sensor 510 may also be attached to translational carriage 502. As shown in FIGS. 5A and 5B, sensor 510 may include a head 512 that rides along an encoder 514. Encoder 514 is attached to track 440. Sensor head 512 and encoder 514 may be an optical positioning sensor, a resistive positioning sensor, or a combination. If sensor 510 is resistance based, then the position of translation carriage 502 along track 440 is determined by the resistance of encoder 514, which operates as a potentiometer, at head 512 where the resistance increases with the travel of translational carriage 502 along track 440. If sensor 510 is optically based, then head 512 may be an optical sensor aligned to measure optical radiation from encoder 514. Sensor 510 can determine the position of translational carriage 502 along track 440 based on the optical inputs.

Figure 6A:
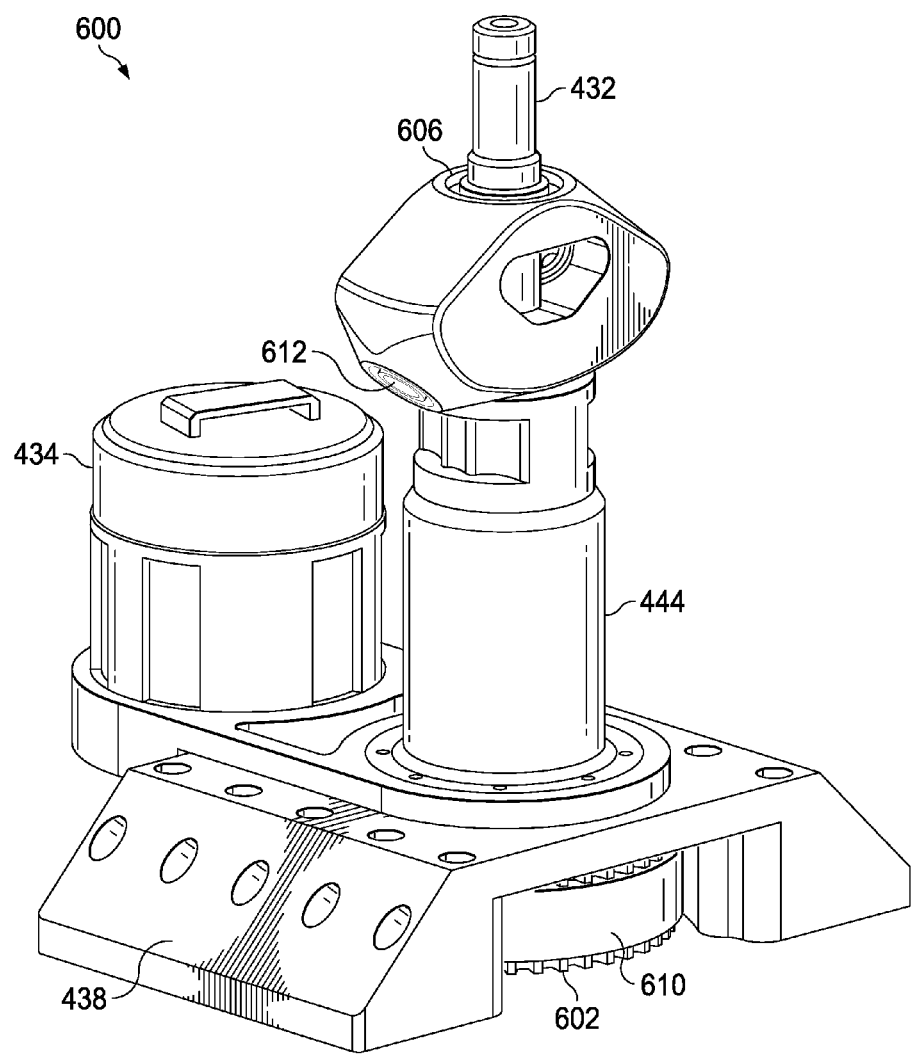
FIGS. 6A and 6B illustrate a shoulder yaw joint of the robot manipulator illustrated in FIG. 4A.
Figure 6C:
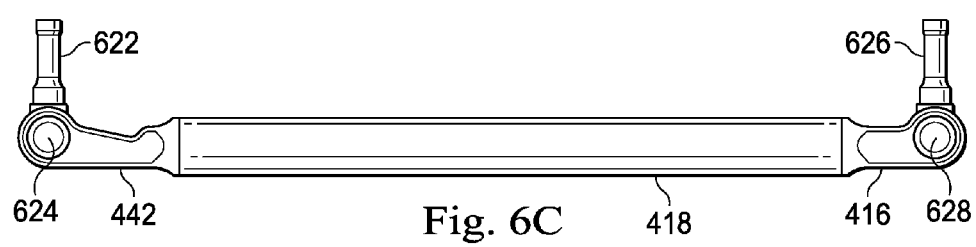
FIG. 6C illustrates a strut that can be utilized in the robot manipulator illustrated in FIG. 4A.
Figure 6B:
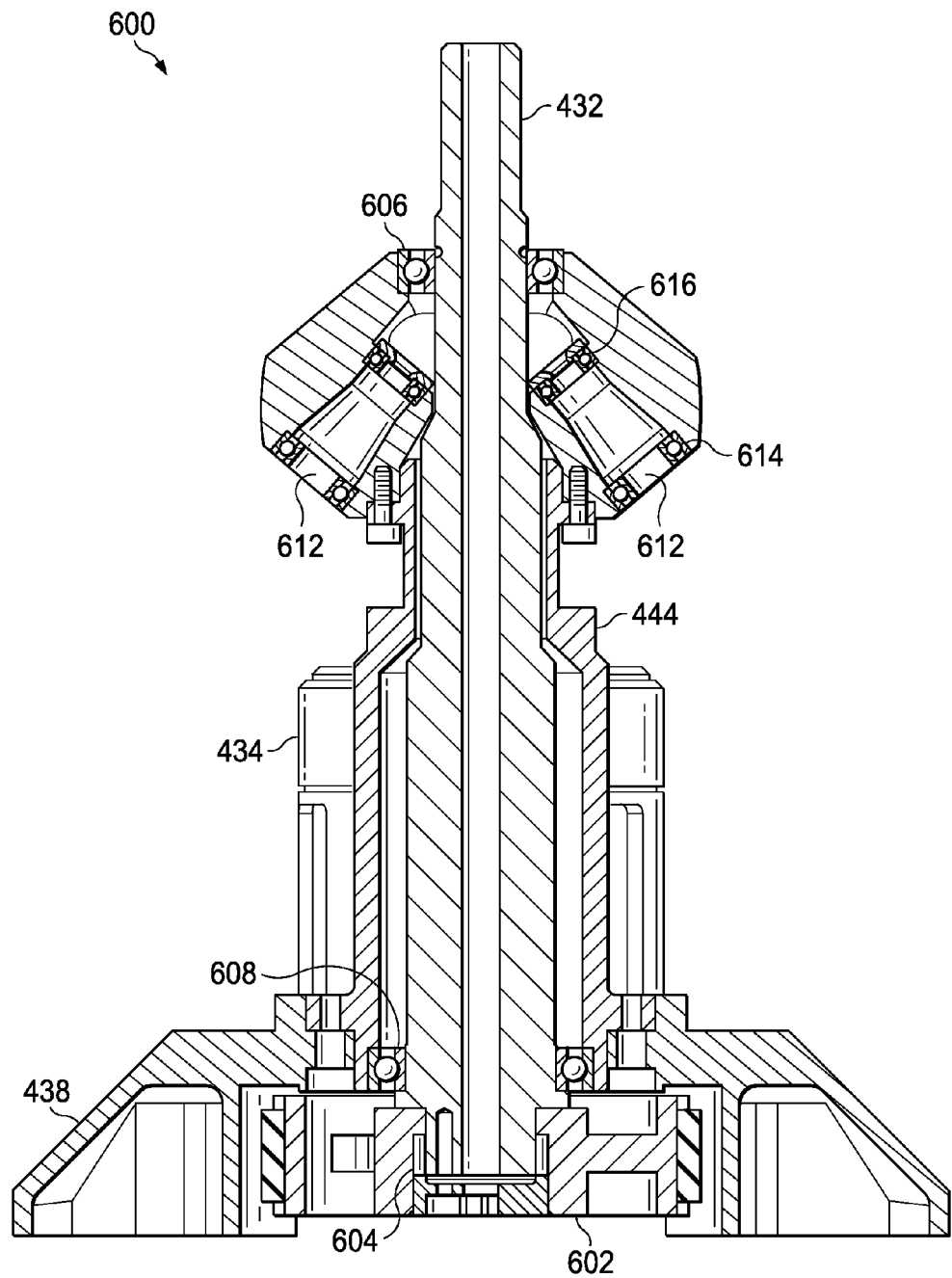

FIGS. 6A and 6B illustrate the shoulder yaw joint 600 of robot 110 as illustrated in FIG. 4A. As shown in FIG. 6A, shoulder yaw joint 600 includes base 438 and support housing 444. Support housing 440 is mounted to, or part of, base 438. Base 438 can then be attached to translation carriage 502, which is illustrated in FIGS. 5A and 5B. Additionally, motor 434 is mounted onto base 438. As further shown in FIG. 6A, shaft 432 passes through support housing 444. A pulley gear 602 is mounted to shaft 432 and coupled to motor 432 with a belt 610. Belt 610 couples pulley gear 602 with pulley gear 436 (see FIG. 4A) of motor 434.

As is further shown in FIG. 6A, support housing 440 includes receivers 612. Receivers 612 mechanically receive joints 442. As shown in FIG. 4A, joints 442 are coupled into receivers 612 such that joints 442 can move with arm 420 while providing a fixed point of attachment on support mount 444.

FIG. 6C illustrates the ends of an embodiment of strut 418. Joint 442 and joint 416 of strut 418 are illustrated. As shown in FIG. 6C, joint 442 includes a shaft 622 that is coupled to strut 418 at pivot 624. In this fashion, strut 418 can be rotated about the long axis of shaft 622 and strut 418 can be rotated in the plane of strut 418 and shaft 622 at pivot 624. Further, joint 416 includes a shaft 626 coupled to strut 418 at pivot 628. Pivot 624 and pivot 628 can be any devices that couple shafts 622 and 626 to strut 418 and allow rotation of shafts 622 and 626 relative to strut 418. In some embodiments, pivots 624 and 628 can be pins through strut 418 and shafts 622 and 626, respectively, or can be ball joints. As illustrated in FIG. 7C and FIG. 4A, joint 442 and joint 416 can be substantially identical.

FIG. 6B illustrates a cross section of shoulder yaw joint 600 through the center of housing support 444 and in a plane that is perpendicular to insertion axis when base 438 is fixed to travel carriage 502. As shown in FIG. 6B, receiver 612 include bearings 614 and 616 and receives shaft 622 of joint 442 in such a way that shaft 622 is fixed along the length of shaft 622 in receiver 612 but allowed to rotate around the length of shaft 622 in receiver 612.

Shaft 432 is inserted through the center of support housing 444. Bearings 606 and 608 provide support and the ability to rotational freedom of shaft 432 along its long axis. As illustrated, pulley gear 602 is coupled to shaft 432 to drive a rotation of shaft 432 around its long axis. Pulley 602 can be locked to shaft 432 with a locking mechanism 604.

FIG. 7A illustrates shoulder pitch joint 700 along with shoulder yaw joint 600. As shown in FIG. 7A, shoulder pitch joint 700 includes arm 420, pitch drive mechanism 422, and struts 418.

Figure 7B:
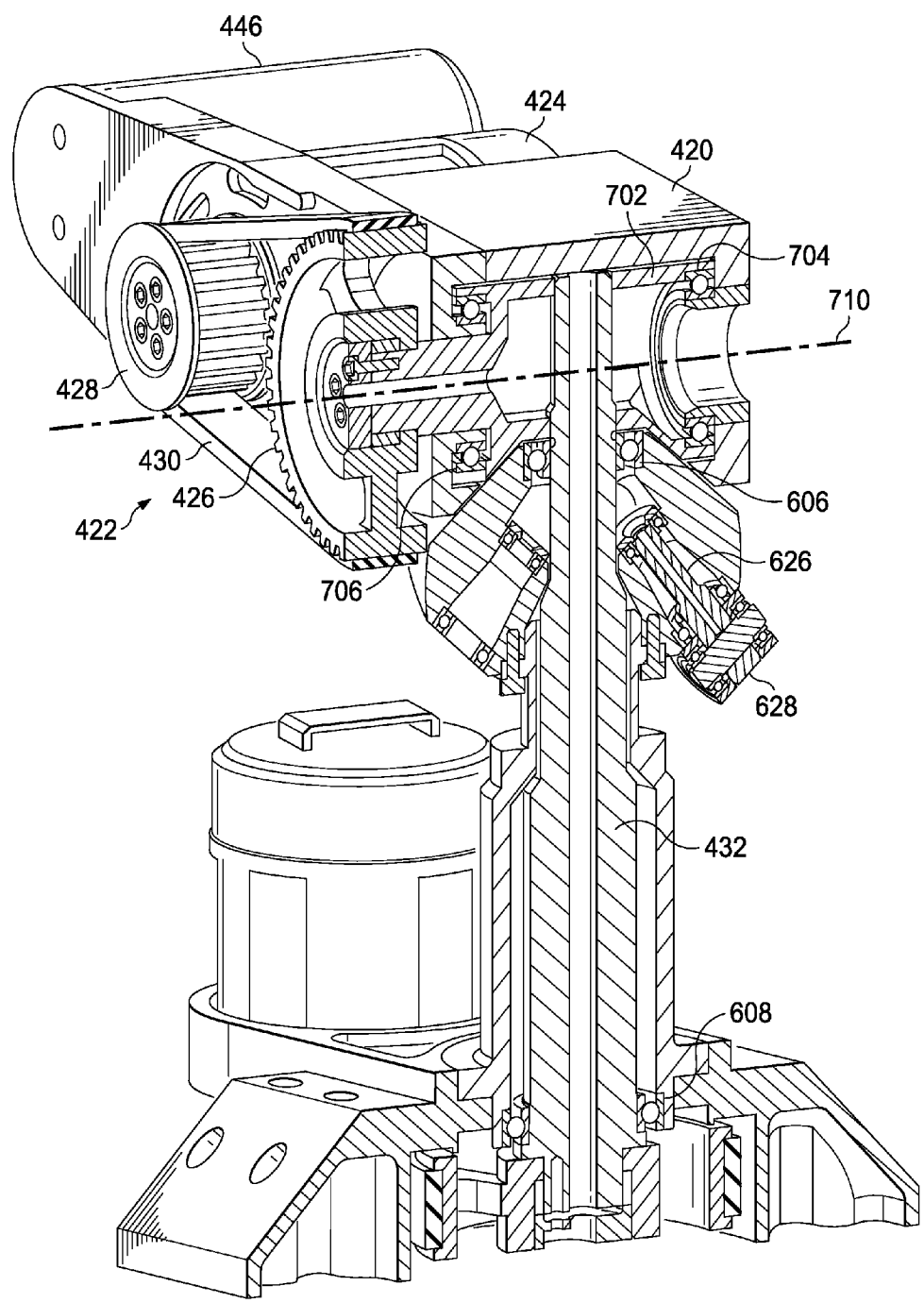
FIG. 7B illustrates a cross section of the shoulder pitch joint illustrated in FIG. 7A.
Figure 7C:
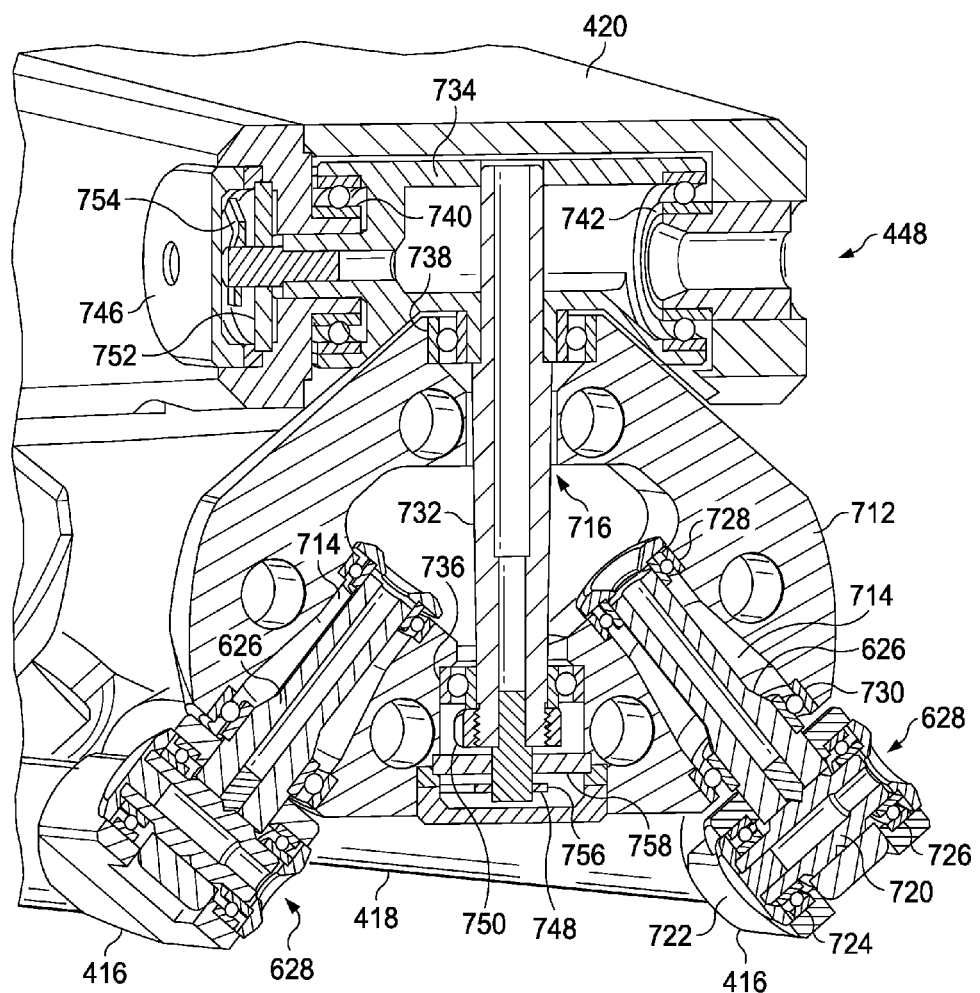
FIG. 7C illustrates a cross section of a connecting joint shown in FIG. 7A and shoulder pitch and yaw position sensors.

FIG. 7B illustrates a cross-sectional view of shoulder yaw joint 600 and shoulder pitch joint 700. As shown in FIG. 7B, shaft 432 includes a cross support 702 that is fixed to shaft 432. Pulley gear 426 is fixed to cross support 702. Arm 420 rotates around axis 710 of cross support 702 on bearings 704 and 706. Pulley gear 428 and motor 424, which is attached to pulley gear 428, are both mechanically coupled to arm 420. Consequently, as pulley gear 428 is rotated, arm 420 rotates around axis 710, raising and lowering wrist 411, which is coupled to the end of arm 420 at wrist mount 712.

As illustrated in FIG. 7A, a wrist mount 712 is mechanically coupled to arm 420 and to struts 418. As shown in FIG. 7A, wrist mount 712 includes receivers 714 to receive shafts 626 of struts 418. Further, wrist mount 712 is coupled to arm 420 at joint 448. As shown in FIG. 7A, wrist mount 712 is coupled to joint 448 at a joint 716 so as to allow rotation of wrist mount 712 when arm 420 is rotated horizontally by shoulder yaw joint 600 or rotated vertically with shoulder pitch joint 700. As a result, wrist mount 712 has a face that remains perpendicular to an insertion direction and also remains vertical.

FIG. 7C illustrates a cross section of joint 448 through wrist mount 712. As illustrated in FIGS. 7A and 7B, joint 448 facilitates the mechanical coupling of wrist mount 712 to arm 420 and struts 418. As illustrated in FIG. 7C, pivot 628 includes a pin 720 that is received in pin receiver 722 at an end of strut 418. Pin 720 rotates on bearings 724 and 726 positioned in pin receiver 722, which is part of strut 418, to allow rotation of pin 720 around its long axis. Pin 720 is attached to shaft 626. Shaft 626 is inserted into receiver 714 as shown in FIG. 7C. Bearings 728 and 730 are positioned to allow rotation of shaft 714 around its long axis.

Joint 448 includes a cross member support 734 and a shaft 732. Cross member support 734 includes a long axis and is positioned at the end of arm 420 such that cross member support 734 can rotate about its long axis riding on the outer diameter of bearings 742 and 740, which are attached to arm 420. Shaft 732 is attached to cross member support 734. Wrist mount is attached to shaft 732 such that it can rotate around a long axis of shaft 732 on bearings 736 and 738. Wrist mount 712 can be retained on shaft 732 with a retainer 750.

The orientation positional determination of wrist mount 712 is provided through positional sensors 746 and 748. Positional sensor 746 provides positional data regarding the shoulder pitch orientation of arm 420. Positional sensor 748 provides positional information regarding the shoulder yaw orientation of wrist mount 712. Positional sensor 746 can include an optical encoder, a potentiometer (resistance) based sensor, or both.

As shown in FIG. 7C, positional sensor 746 includes a first part 752 that is fixed on arm 420 and a second part 754 that is fixed on cross member support 734. As such, when cross member support 734 is rotated with respect to arm 420, first part 752 is rotated with respect to second part 754. In the case where positional sensor 746 includes a potentiometer based sensor, then one of the first part 752 or the second part 754 includes a sweeper and the opposite of the first part 752 or the second part 754 includes a resistive element that engages with the sweeper. The resulting indication of total resistance indicates the angular orientation of first part 752 with respect to second part 754. Similarly, in the case where positional sensor 746 includes an optical sensor, then one of first part 752 or second part 754 includes an optical encoder and the opposite one of first part 752 or second part 754 includes an optical head for reading the optical encoder. Again, the angular orientation of first part 752 with respect to second part 754 can be determined by the resulting information.

Similarly, shoulder yaw positional sensor 748 includes a first part 758 that is fixed on wrist mount 712 and a second part 756 that is fixed to shaft 732. As wrist mount 712 rotates with respect to shaft 732, which it will do when the shoulder yaw joint 600 is actuated, then first part 758 is rotated with respect to second part 756. Again, in the case where positional sensor 748 includes a potentiometer based sensor, then one of the first part 758 or the second part 756 includes a sweeper and the opposite of the first part 758 or the second part 756 includes a potentiometer that engages with the sweeper to determine from the measured resistance the angular orientation of first part 758 with respect to second part 756. Similarly, in the case where positional sensor 748 includes an optical sensor, then one of first part 758 or second part 756 includes an optical encoder and the opposite one of first part 758 or second part 756 includes an optical head for reading the optical encoder to determine the angular orientation of first part 758 with respect to second part 756.

Figure 8A:
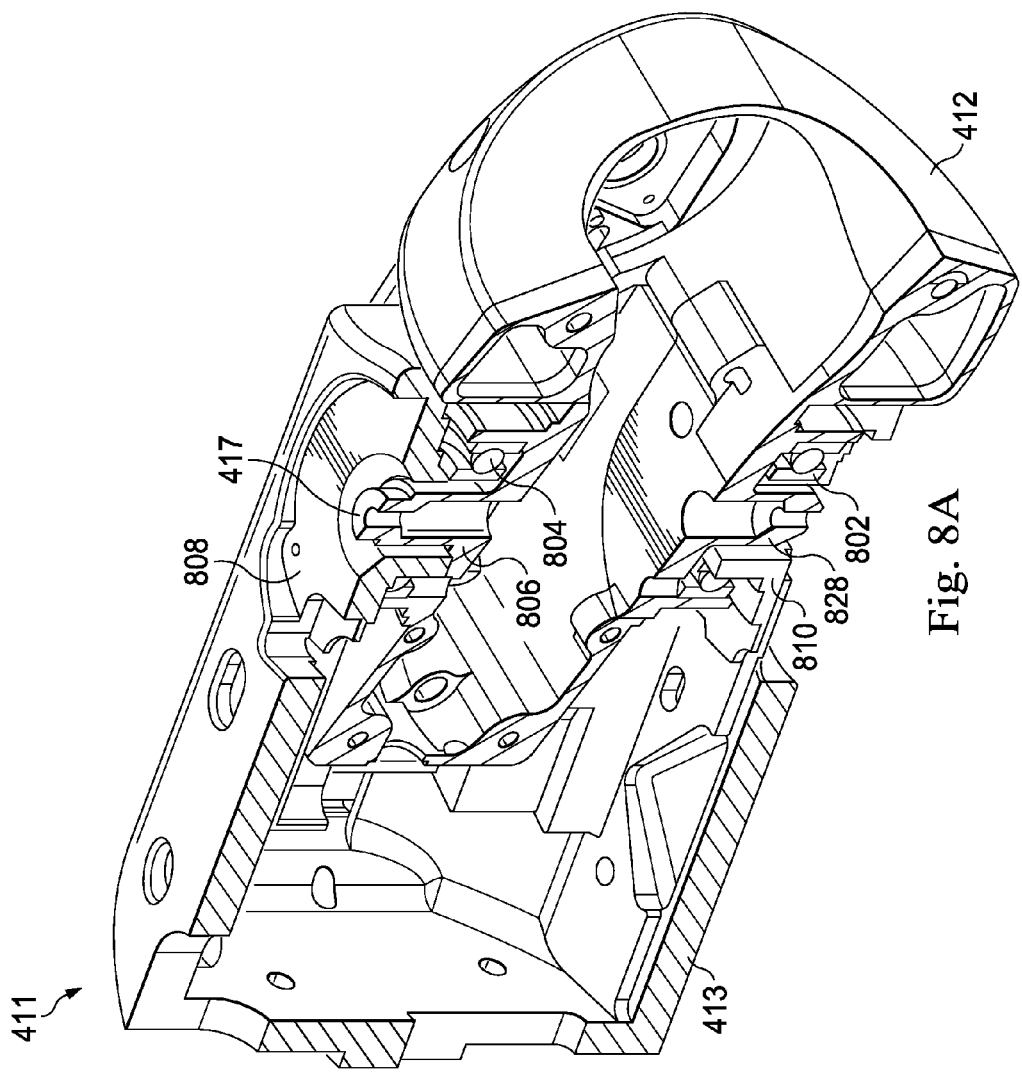
FIGS. 8A, 8B, 8C, 8D, and 8E illustrate embodiments of aspects of a yaw-pitch-roll wrist of the robot manipulator illustrated in FIG. 4A.

FIG. 8A illustrates yaw of wrist 411. Section 413 of wrist 411 is mechanically coupled to wrist mount 712 shown in FIG. 7A. Section 412 includes pins 806 and 828 that can protrude through matching holes in surfaces 808 and 810, respectively, to form yaw pivot 417. As shown in FIG. 8A, bearings 802 and 804 can be provided around pins 806 and 828 against surfaces 808 and 810, respectively. As such, section 412 can be rotated around yaw pivot 417.

Figure 8B:
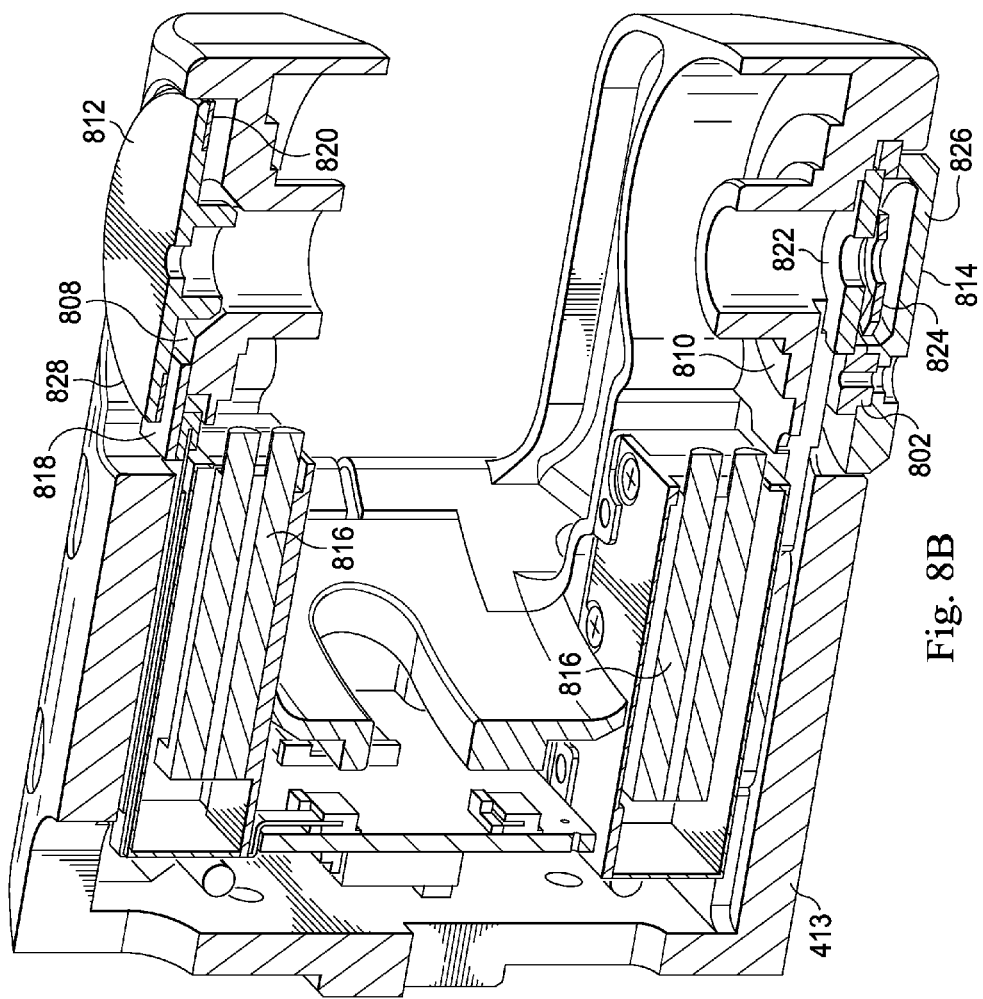

FIG. 8B illustrates further aspects of section 413. As shown in FIG. 8B, section 413 includes one or more motors 816. Motors 816 provide the force to affect a rotation of section 812 as shown in FIG. 8A around yaw pivot 417. Further shown in FIG. 8B, an optical position sensor 828 and a resistive position sensor 826 both provide information regarding the yaw rotational orientation of section 212 with respect to section 213, as illustrated in FIG. 8A.

Optical position sensor 828 includes an optical head 818 and an encoder 820. As shown in FIG. 8B, encoder 820 is placed on a mount 812, which attached to pin 806. In which case, optical head 818 reads encoder 820 and the angular orientation of encoder 820 with respect to head 818 can be determined.

Resistive sensor 826 includes a sweeper 824 and resistive element 822. Resistive element 822 can be fixed on section 413. Sweeper 824 can be fixed on a mount 814, which is attached and fixed to pin 828. Again, the angular orientation of sweeper 824 on resistive element 822, and therefore the angular orientation of section 412 with respect to section 413, can be determined by the resistance measured at sweeper arm 824.

Figure 8C:
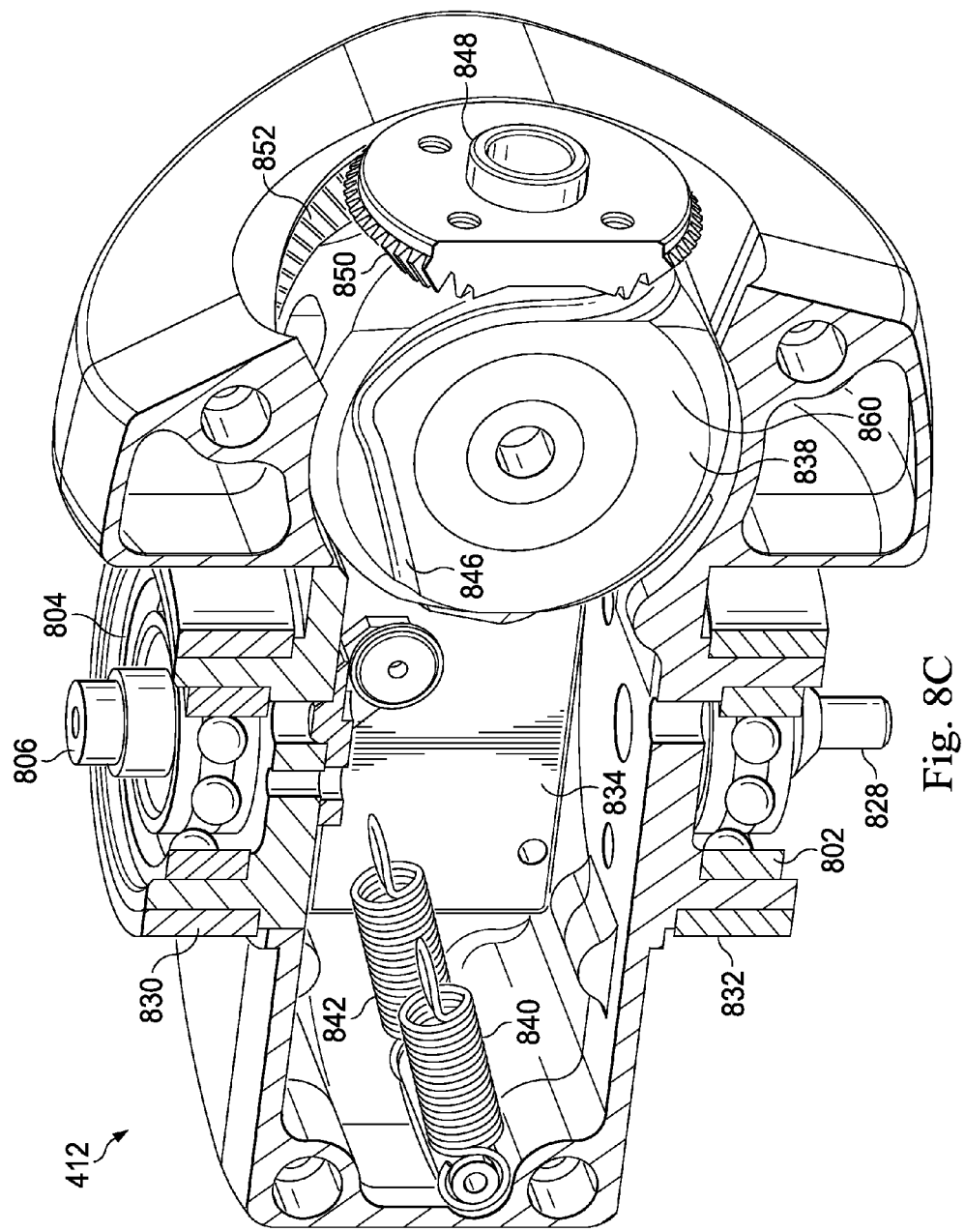

FIG. 8C further illustrates section 412 of wrist 411. As shown in FIG. 8C, ceramic wheels 830 and 832 provide surfaces on which motors 816 can operate to affect the yaw rotation of section 412 with respect to section 413. Pitch and roll actuation is performed by gear apparatus 838. Gear apparatus 838 engages a gear 850 that is part of mount 410. Gear 850 is mechanically coupled to a shaft 848. As shown in FIG. 8C, gear apparatus 838 is partially driven by motor 834, as is discussed further below. Roll and pitch motions of shaft 848 are accomplished through differential drive of gear apparatus 838.

As is further shown in FIG. 8C, gear apparatus 838 includes a core 860. Further, a wire (not shown) can be attached between springs 840 and 842 and through wire run 846 of core 860. Such an arrangement provides for a spring-loaded counter balance to the pitch motion of shaft 848 and mount 410.

Figure 8D:
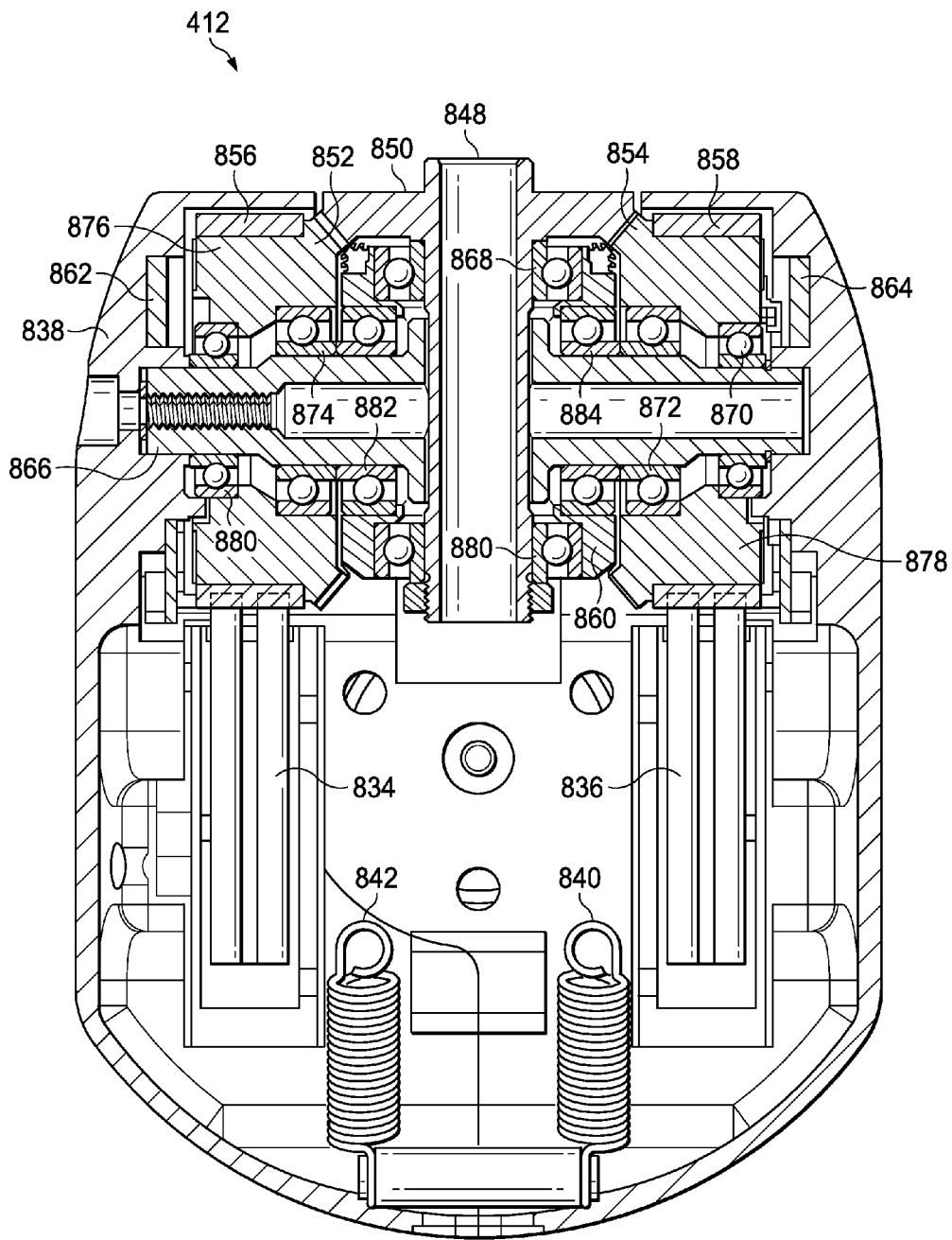

FIG. 8D illustrates a cross section of section 412 that illustrates the operation of gear apparatus 838. As illustrated in FIG. 838, gear apparatus 838 includes a shaft 866 that is fixed with section 412. Shaft 866 passes through core 860. Core 860 receives shaft 848 and shaft 866 such that shaft 848 passes through shaft 866 in core 860. Further, wheels 876 and 878 are arranged to rotate about shaft 866. Wheel 876 rotates on bearings 860 and 874 while wheel 878 rotates on bearings 870 and 872. A gear 852 is mechanically attached to wheel 876 while a gear 874 is mechanically attached to wheel 878. Gears 852 and 874 engage gear 850, which is attached to shaft 848.

Bearings 868 and 880 allow shaft 848 to rotate within core 860. Shaft 848 and core 860 can then rotate around shaft 866 on bearings 882 and 884. As such, shaft 848 can be rotated around its length, which is the wrist roll motion, and shaft 848 can be tilted around the length of shaft 866, which is the wrist pitch motion.

Wheel 876 includes a ceramic disc 856 and wheel 878 includes a ceramic disc 858. Ceramic discs 856 and 858 can be engaged by motors 834 and 836, respectively, to rotate wheels 878 and 876 (and consequently gears 852 and 854) around shaft 866. As illustrated in FIG. 8D, if wheels 876 and 878 are rotated by motors 834 and 836, respectively, in the same rotational sense, then shaft 848 is rotated around shaft 866 and a pitch rotation is affected. If wheels 876 and 878 are rotated in opposite rotations, then shaft 848 is rotated around its axis and a roll rotation is affected.

Figure 8E:
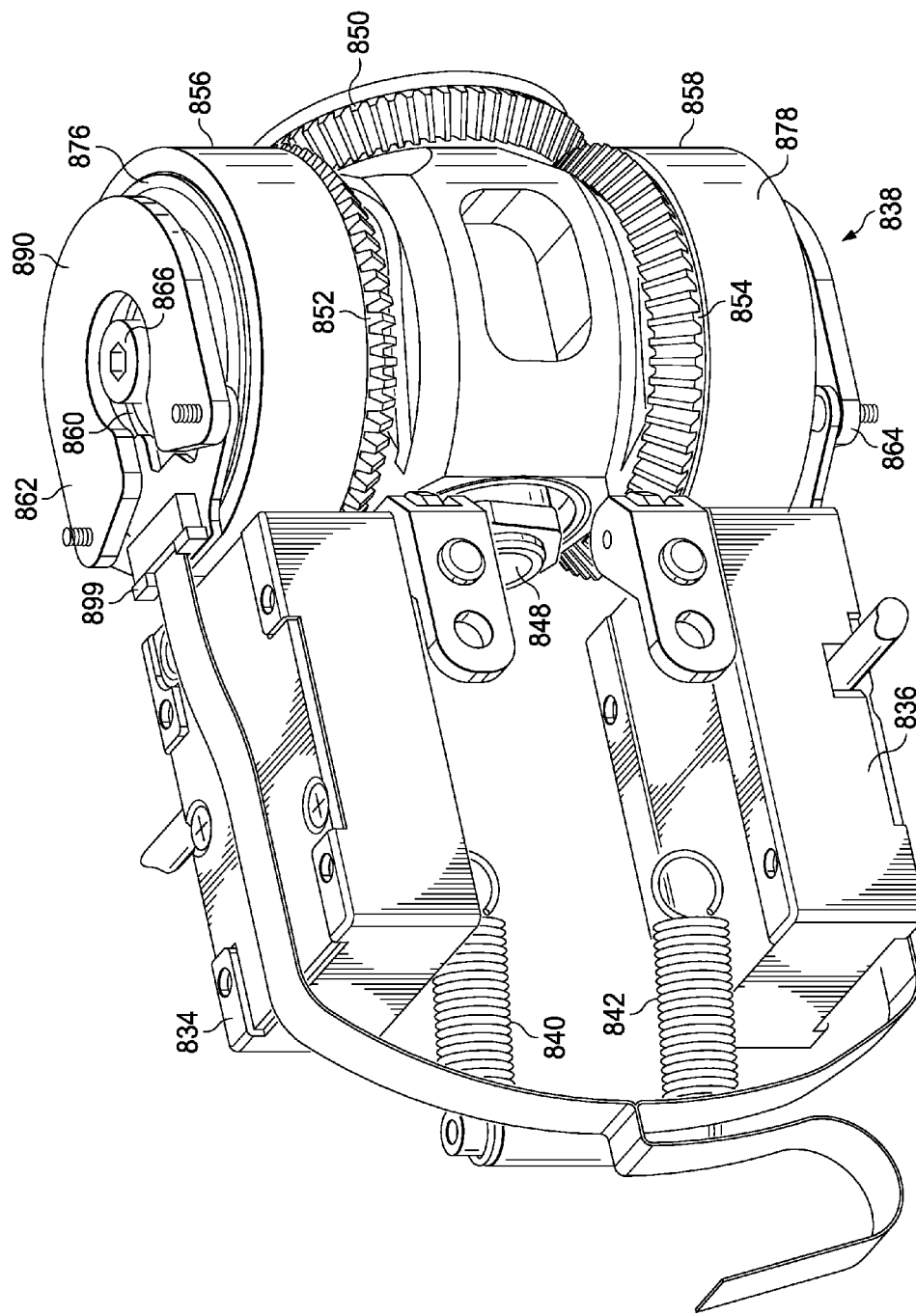

FIG. 8E further illustrates gear apparatus 838. As is illustrated, motor 834 engages ceramic disk 856 while motor 836 engages ceramic disc 858. During rotation, gears 852 and 854 engage gear 850 as described above. When both gears 854 and 852 are driven in the same rotation, then core 860 and consequently shaft 848 is rotated. When gears 854 and 852 are driven in opposite rotations, then gear 850 is rotated and shaft 848 is rotated about its long axis.

FIG. 8E further illustrates positional sensors 862 and 864. Positional sensors 862 and 864 provide information regarding the rotational positions of wheels 876 and 878, respectively. From the rotational positions of each of wheels 876 and 878, the pitch and roll positions of shaft 848 and gear 850 can be determined.

Figure 8F:
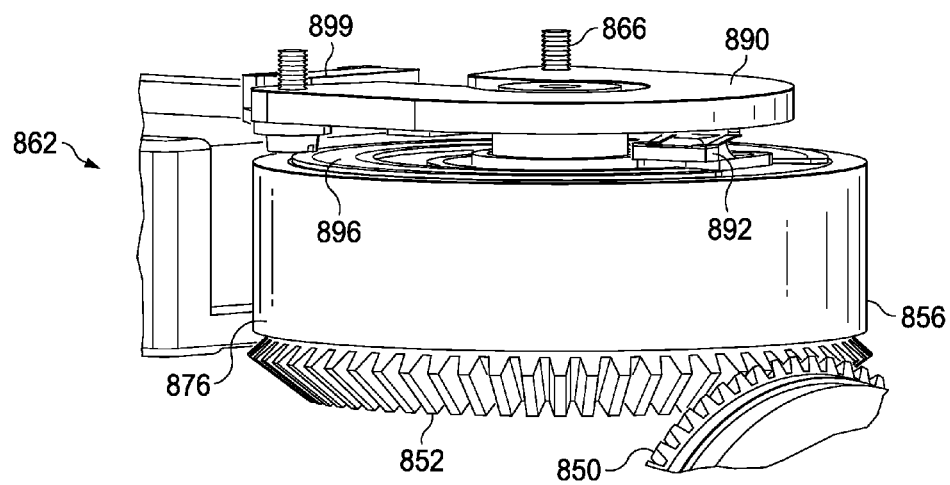
FIGS. 8F, 8G, and 8H illustrate a positional sensor utilized with the wrist illustrated in FIGS. 8A, 8B, 8C, 8D, and 8E.

FIG. 8F illustrates positional sensor 862. In some embodiments, positional sensor 864 can be substantially the same as is positional sensor 862. In general, positional sensors 862 and 864 can be any sensor that provides the rotational position of wheels 876 and 878, respectively. Positional sensor 862 illustrated in FIG. 8F includes both an optical sensor and a resistive sensor.

Figure 8G:
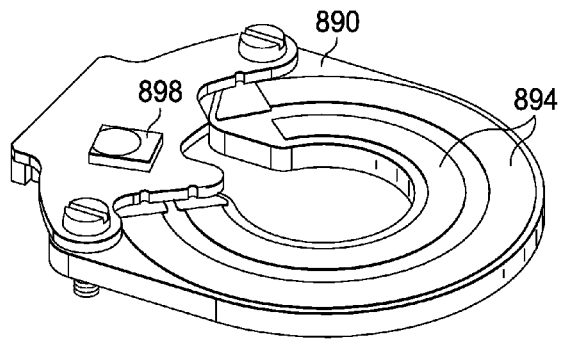
Figure 8H:
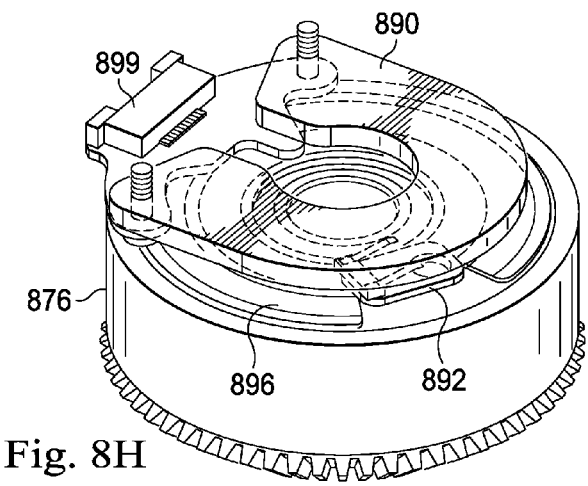

As shown in FIG. 8F, positional sensor 862 includes a fixed portion 890 that is fixedly mounted to section 412. As shown in FIG. 8G, fixed portion 890 includes an optical head 898 and resistive potentiometer tracks 894. FIG. 8G illustrates fixed portion 890, showing the side of fixed portion 890 that faces wheel 876. As shown in FIG. 8H, signals from potentiometer tracks 894 and from optical head 898 are input to an electronic connector 899, which provides signals related to the two measurements of position. As such, signals from optical head 898 and resistive sweeps 892 are supplied to other electronics as is illustrated in FIG. 8E.

FIGS. 8F and 8H illustrate the position of resistive sweep 892, which electrically engage potentiometer track 894. As shown in FIG. 8H, resistive sweep 892 is provided on wheel 876 and provide electrical connection between potentiometer tracks 894 on fixed portion 890. Optical head 898 reads data from an encoder 896 that, as shown in FIG. 8H, is provided on wheel 876. Encoder 896 and sweep 892 are opposite fixed portion 890. Sweep 894 and encoder 896 can be provided on wheel 876 to reflect the rotational range of motion of wheel 876 with respect to fixed portion 890. In some embodiments, wheel 876 does not rotate a full 360 degrees of motion with respect to fixed portion 890. Positional sensor 862, then, provides both resistive based positional information and optically based positional information.

Figure 9A:
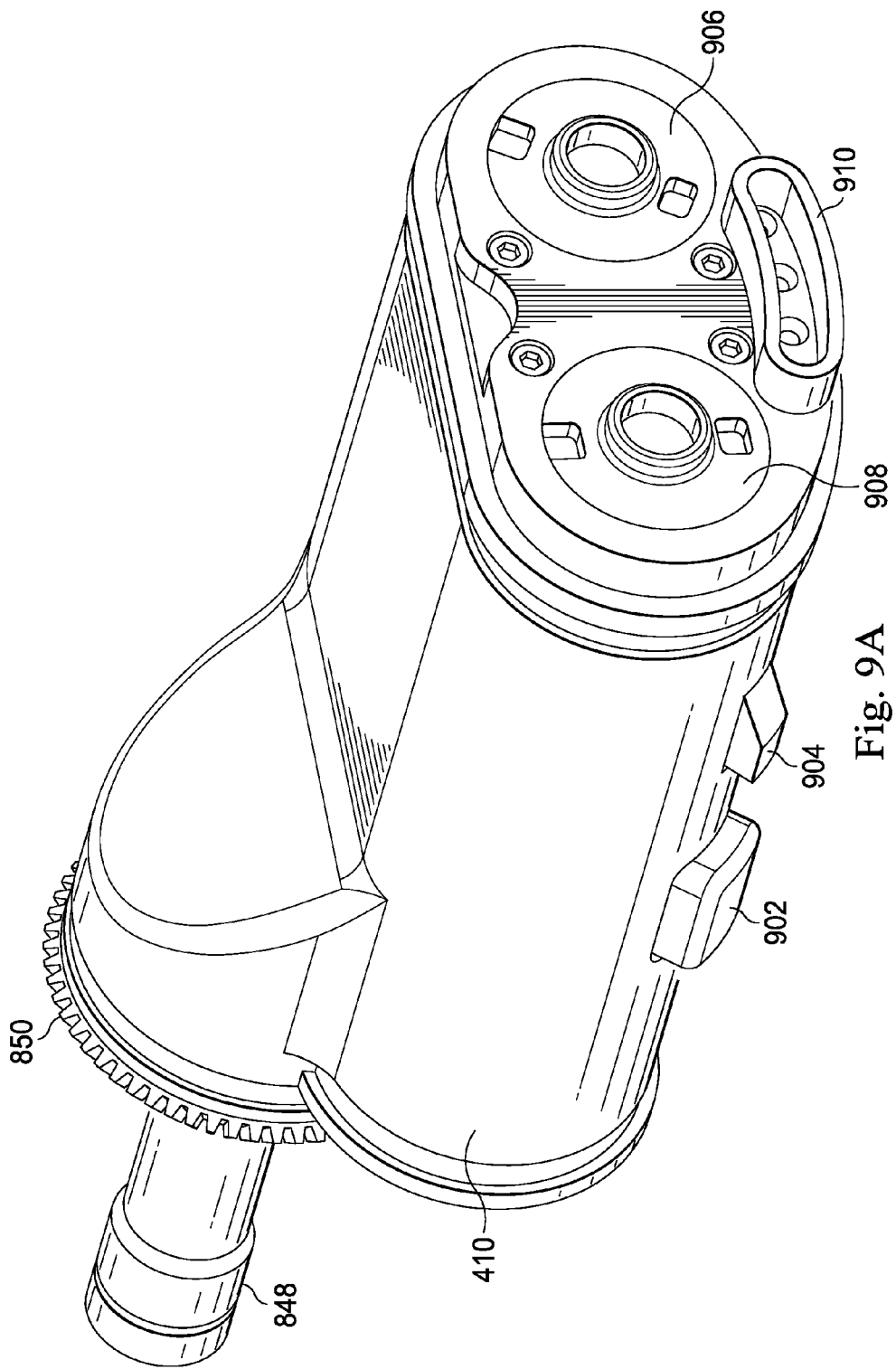
FIGS. 9A, 9B, and 9C illustrate embodiments of a carriage mount of the robot manipulator illustrated in FIG. 4A.

FIG. 9A illustrates an embodiment of a mount 410. As illustrated in FIG. 9A, mount 410 includes shaft 848 and gear 850. As discussed previously, shaft 848 and gear 850 are coupled with wrist 411. Mount 410 includes drives 906 and 908 and electrical connector 910. As discussed above, drives 906 and 908 are utilized to actuate features of needle based instrument 210. Electrical connector 910 allows communications with a process or data stored in needle based instrument 210. In many cases, sterile adaptor 414 is coupled to mount 410 and needle based instrument 210 is coupled to sterile adaptor 414. Mount 410 can include a button 920 and catch 904 to receive sterile adaptor 414.

Figure 9B:
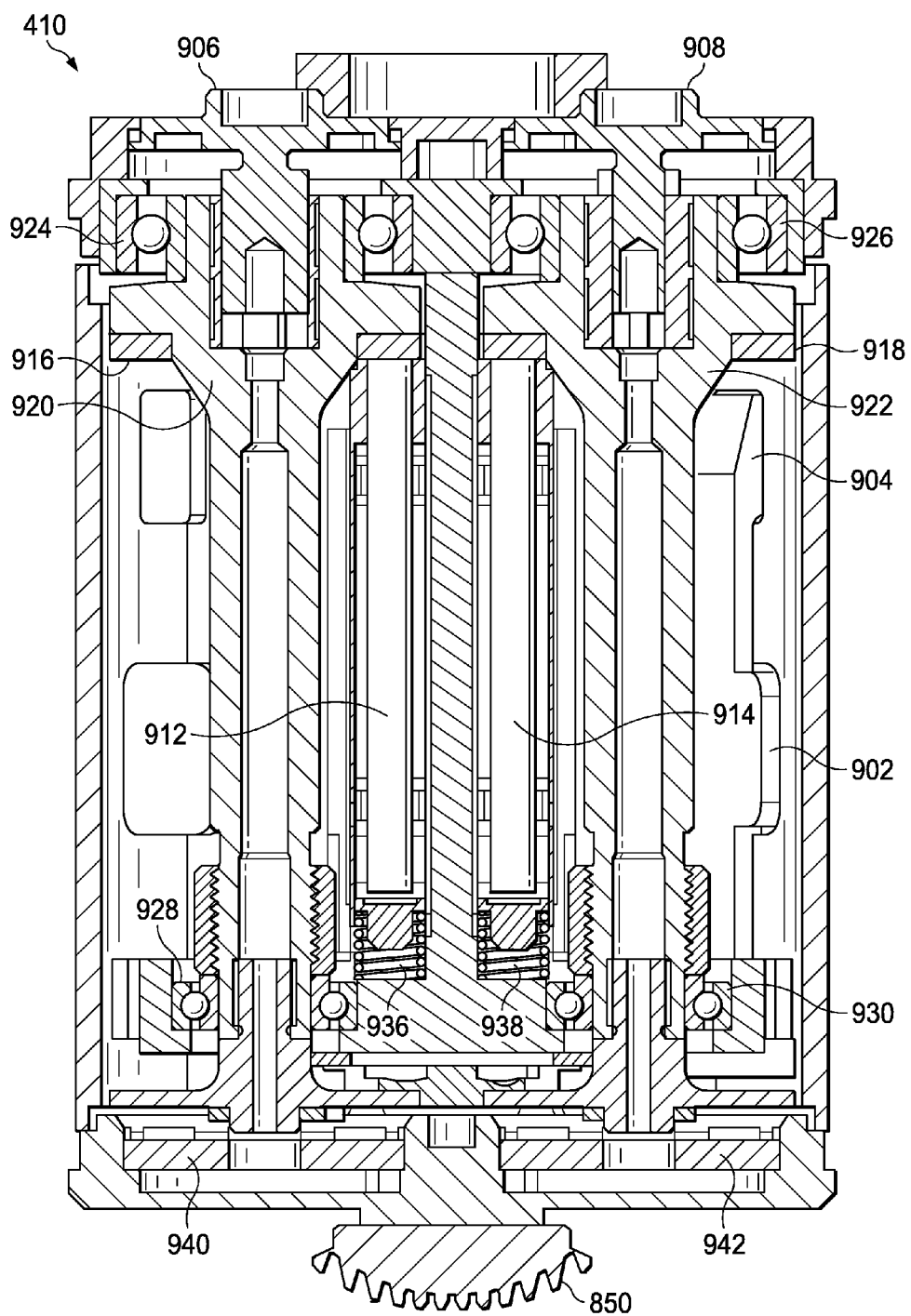

FIG. 9B illustrates a cross section through drives 906 and 908 of mount 410. As shown in FIG. 9B, drive 906 is coupled to a shaft 920. Drive 908 is coupled to a shaft 922. A motor 912 engages a ceramic disk that is mounted on shaft 916. When motor 912 is engaged against ceramic disk 916, shaft 920 is rotated. Shaft 920 is rotated on bearings 928 and 924. Similarly, motor 914 engages a ceramic disk 918 that is coupled to shaft 922. When motor 914 is engaged, shaft 918 is rotated on bearings 926 and 930.

In some embodiments, there may be spring loading between drive 906 and shaft 920 and between drive 908 and shaft 922. In that fashion, drives 906 and 908 may absorb motion from needle based instrument 210 or sterile adaptor 414 during use.

Additionally shaft 920 may engage positional sensor 940 and shaft 922 may engage positional sensor 942. Positional sensors 940 and 942 provide rotational position information regarding drives 906 and 908.

Figure 9C:
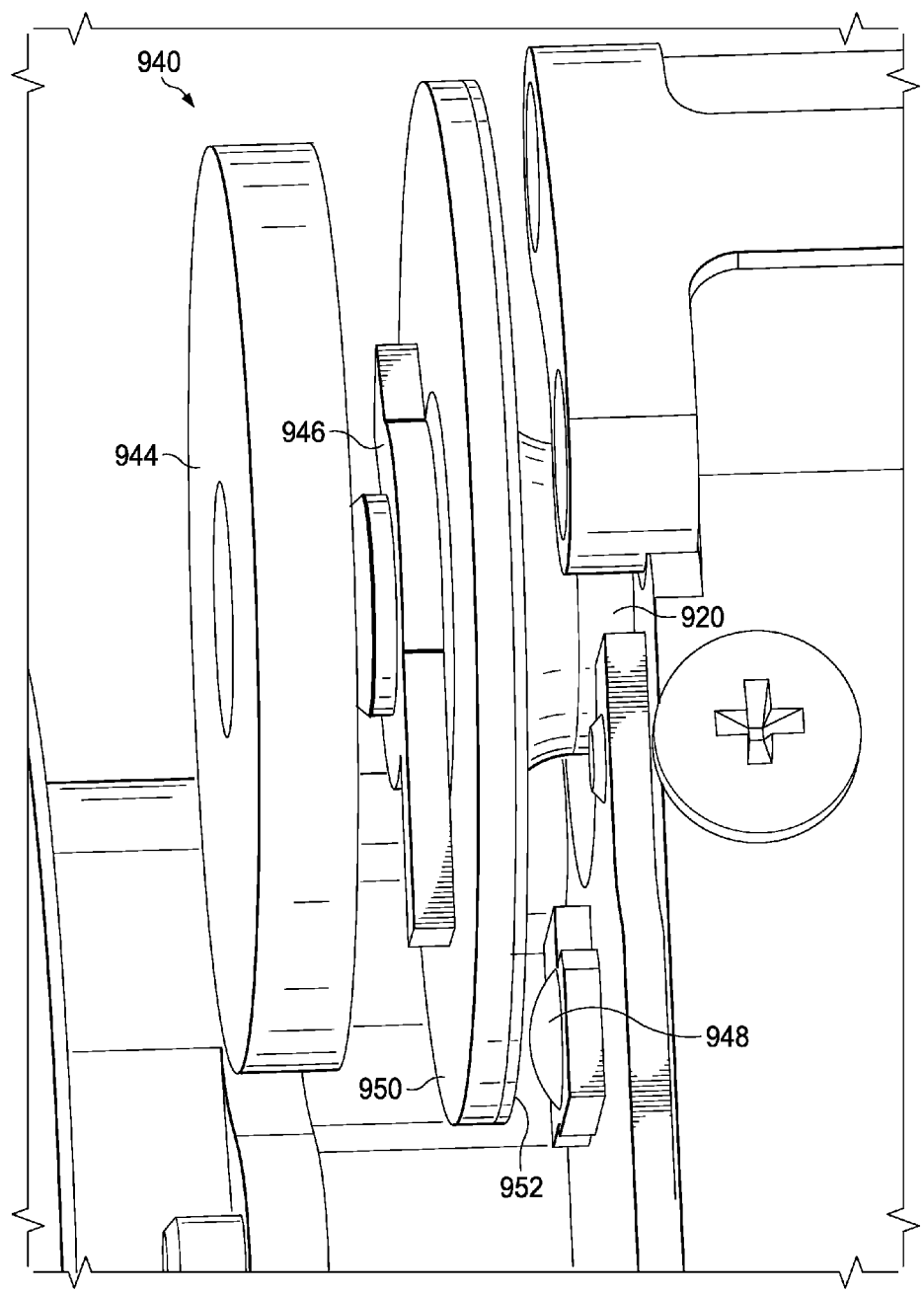

FIG. 9C illustrates an example embodiment of positional sensor 940. Positional sensor 942 may be substantially similar to positional sensor 940. In the embodiment shown in FIG. 9C, positional sensor 940 includes both a resistive sensor and an optical sensor. A disc 950 is engaged with shaft 920 so that it turns with shaft 920. Optical head 948 provides positional information by receiving optical information from an encoder 952 that is fixed to disc 950. Further, a resistive sweep arm 946 is also mounted on disc 950. Resistive sweep arm 946 electrically engages a potentiometer resistive element 944 that is fixed with mount 410. As such, positional information can be determined from the resistance signal received from sweep arm 946 and potentiometer resistive element 944 and from optical data determined by optical head 948 and encoder 952.

Figure 10A:
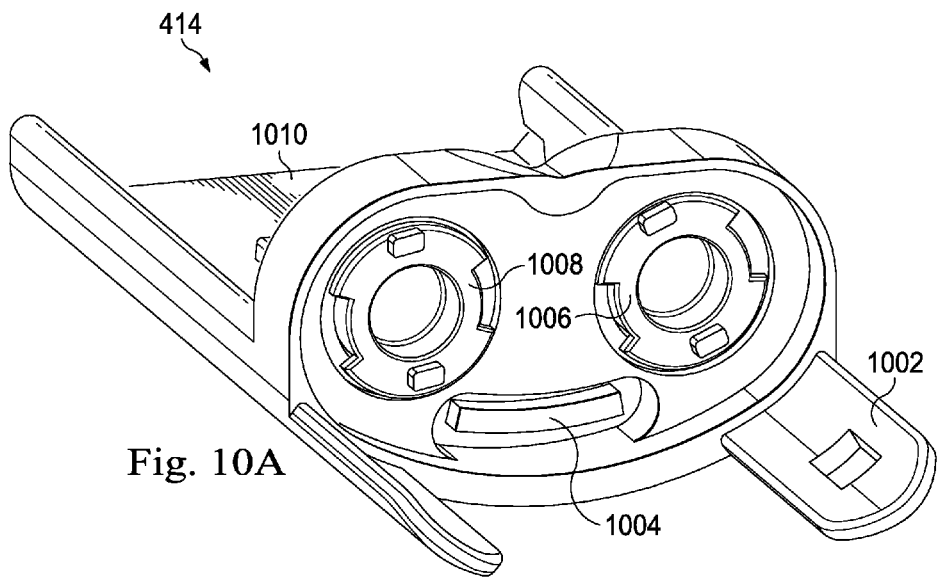
FIGS. 10A and 10B illustrate a sterile adaptor that can be utilized with the carriage mount illustrated in FIGS. 9A, 9B, and 9C.
Figure 10B:
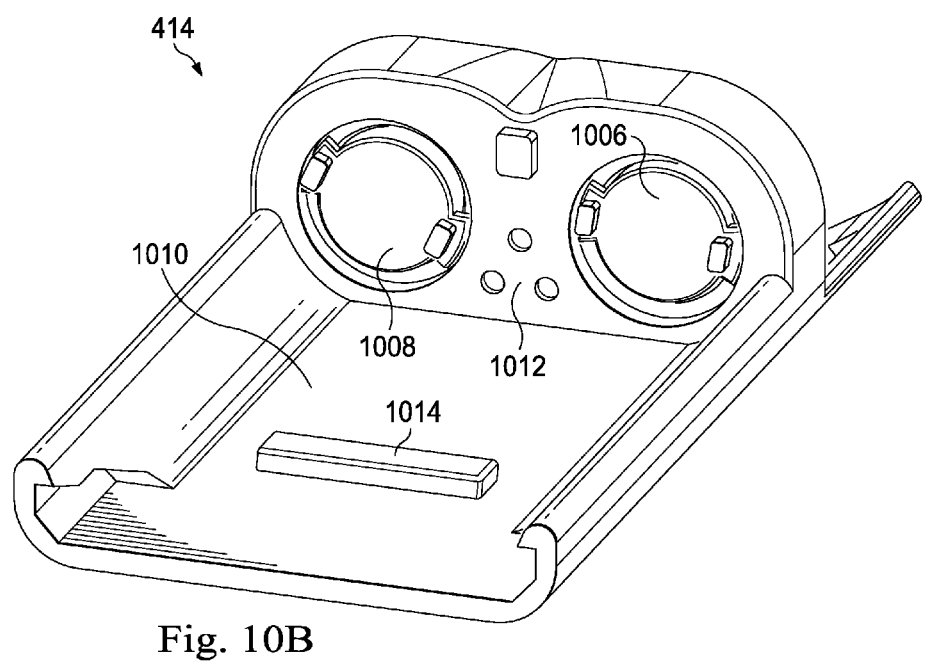

FIGS. 10A and 10B illustrate a sterile adaptor 414 that can be utilized with mount 410. As shown in FIG. 10A, sterile adaptor 414 includes an adaptor 1002 that engages latch 904 of mount 410. Further, a drive 1006 engages drive 906 of mount 410 and a drive 1008 engages drive 908 of mount 410. Electrical connector 1004 of sterile adaptor 414 connects with electrical connector 910 of mount 410. Sterile adaptor 414 also includes a cradle 1010 to receive needle based device 210.

As shown in FIG. 10B, needle based device 210 may couple with drives 1006 and 1008. Electrical connector 1012 is coupled with electrical connector 1004. Further, a latch 1014 in cradle 1010 may fix needle based device 210 into sterile adaptor 414.

As discussed above, vertical positioning of wrist 411 and mount 410 is provided through a 3-D parallelogram formed by arm 420 and struts 418 and driven by motor 424 through drive mechanism 422. The parallelogram helps minimize torques at the other joints and also keeps section 413 of wrist 411 horizontally oriented and substantially aligned along track 440. As shown in FIG. 4A, arm 420 is counterbalanced with weight 446 for ease of motion. As described above, wrist 411 is a yaw-pitch-roll wrist.

Needle insertion into the patient is performed by a coordinated motion of the entire robot 110, as opposed to the motion of one dedicated joint in robot 110. In some embodiments, robot 110 is confined to operate in the space between the patient's legs within the bore of an MRI instrument, as is illustrated in FIG. 2. Consequently, in some embodiments of robot 110 the size of the components and the allowable DOF motions can be arranged within that confined space.

Embodiments of robot manipulator 110 can be provided that utilize a variety of combinations of DoFs. As an example, and not to be limiting, a particular combination of DoFs is provided below. The horizontal/axial motion along track 440 can be about 215 mm. The horizontal/transverse at wrist 411 by shoulder yaw joint 600 can be about ±115 mm. The vertical motion of wrist 411 actuated by shoulder pitch joint 700 can be about ±125 mm. The vertical rom center can be about 177.5. The tilt or elevation parameter can be +30° and −15°. The pan or azimuthal motion imparted by wrist 411 can be ±15°. The insertion distance imparted by robot 110 can be 150 mm. The roll imparted by wrist 411 can be ±135°. In some embodiments of instrument 210, the sheath retraction and laser advance motion can be 25 mm and the roll continuous. The needle insertion force can be about 40N with a needle insertion velocity 50 mm/s.

All of the joints can be driven by piezo-electric motors such as those produced by Nanomotion. Motors 424 and 434 can be piezo-electric motors, for example as described in U.S. Utility application Ser. No. 13/767,801. The motor in base 438 can be, for example, a linear piezoelectric motor. In some embodiments, linear motors 506 (FIG. 5A) can be two Nanomotion HR8 motors. Wrist Yaw motors 816 (FIG. 8B) can, for example, each can be two HR2 motors. Wrist pitch-roll motors 834 and 836 can be single Nanomotion HR2 motors. Motors 912 and 914 in mount 410 (FIG. 9B) can be formed of individual piezoelectric elements mounted within the housing of mount 410.

Figure 11:
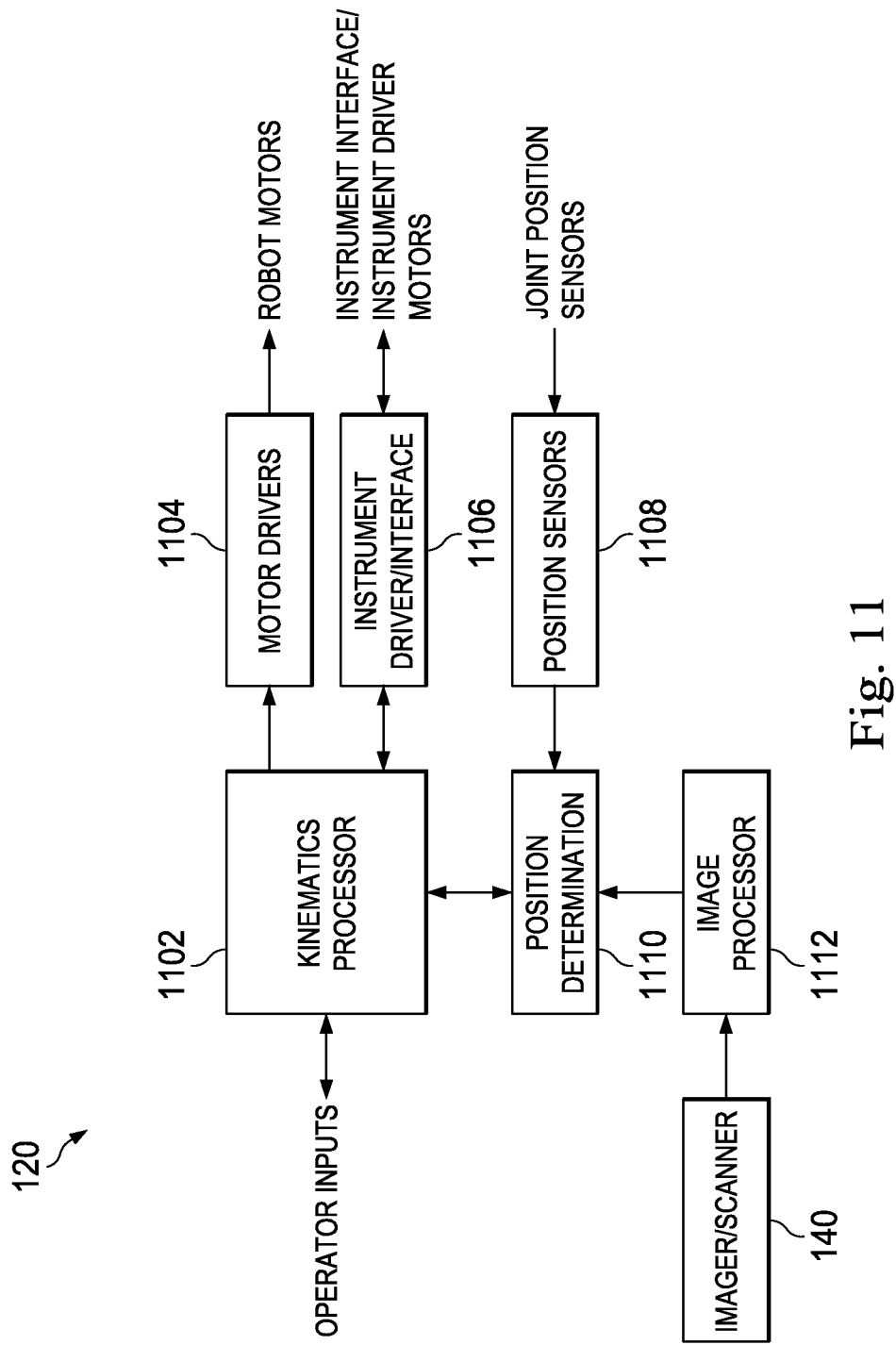
FIG. 11 is a block diagram that illustrates a controller for the robot manipulator.

FIG. 11 is a block diagram that illustrates the functionality of controller 120. As shown in FIG. 6, operator inputs are received in controller 120 at a kinematics processor 1102. The operator inputs originate at console 130 as a result of an operator instructions of a procedure to be executed by robot 110. Kinematics processor 1102 determines the motion of robot 110 and provides appropriate signals to motor drivers 1104. Motor drivers 1104 provide the driving signals to each of the motors on robot 110. Kinematics processor 1102 also provides signals to instrument driver and interface 1106, which drives motors 912 and 914 providing inputs to instrument 210. In some embodiments, instrument 210 provides input information to interface 1106. This input information, for example, can include instrument type, instrument history, and instrument operational parameters. The information provided by interface 1106 is provided to kinematics processor 1102 and to console 130 in order that proper motions of robot 110 and instrument 210 can be coordinated.

Position determination 1110 determines and tracks the position of robot 110. Position determination 1110 monitors the control signals sent from kinematics processor 1102 to motor drivers 1104 and integrates those motions to determine the orientation of each joint of robot 110 based on the activity of each motor. As such, joint position sensing can be primarily based on incremental encoders as discussed above in position determination 1110. In some cases, sensors such as resistive potentiometers or optical positional sensors can provide signals to positions sensors 1108. Positions sensors 1108 monitors the sensors on robot 110 and provides real-time absolute position information to position determination 1110, which can be utilized to determine the start-up position of robot 110 and for error checking of the position as determined incrementally. As discussed above, the motors in robot manipulator 110 are piezoelectric motors. The relative positions of these motors with respect to their start-up positions can be determined in controller 120 based on the control signals that controller 120 sent to them. In some embodiments, resistive or optical positioning sensors can be placed on robot 110 to provide start-up positions and error checking.

In some embodiments, position determination 1110 can also receive data from an image processor 1112. Image processor 1112 receives images from scanner 140. Image processor 1112 may determine the location of robot manipulator 110 based on an image of instrument 210. In some embodiments, image processor 1112 may determine the positioning of instrument 210 based on fiducials mounted on instrument 210 that are particularly detectable in an image from scanner 140.

Materials utilized in building robot 110 are non-magnetic and can be, for example, aluminum, titanium, and engineering plastics such as Ultem, PEEK, or Delrin. Carbon Fiber may be utilized in specific areas. Linear bearings utilized in base 440 may be ceramic bearings. Ball bearings utilized in other motions of robot 110 may be ceramic bearings or may be an amagnetic hybrid bearing. Encoders utilized in positional sensors can utilize optical chips, for example, from Avago Technologies. Most of the potentiometers utilized in the positional sensors can be obtained from Spectrum Controls.

As illustrated above, robot 110 is a compact manipulator for positioning and driving needles for targeted diagnostics and therapy. Instrument 210 can be, for example, a biopsy instrument, a laser ablation instrument, a treatment delivery instrument, or any other needle-based instrument. Full Cartesian positioning and orientation is provided to instrument 210 with multiple driving inputs through mount 410 and motors 413 to control individual DoFs within instrument 210, for example rotation. Once robot 110 is initially positioned, needle insertion is driven by a coordinated motion of the joints of robot 110. In initially positioning, for example, end effector mount 410 can be positioned to minimize patient interference.

Instrument 210 is discussed in more detail in U.S. Provisional Application No. 61/599,300. Instrument 210 can be mounted to a sterile adaptor 414 before being mounted to effector mount 410. Keying and locking of the sterile adaptor and instrument 210 are discussed in U.S. Provisional Application No. 61/599,300.

Further, a sterile interface can be provided by a drape over robot 110. An interface between instrument 210 and robot 110 allows controller 120 to determine information about instrument 210, for example, instrument ID, serial number, geometric parameters, and uses. In some embodiments, instrument 210 can included embedded fiducials for localization within the imager.

The above detailed description is provided to illustrate specific embodiments of the present invention and is not intended to be limiting. Numerous variations and modifications within the scope of the present invention are possible. The present invention is set forth in the following claims.

What is claimed is:

1. An instrument manipulator, comprising:
   a track;
   a translational carriage coupled to ride along the track, the translational carriage being propelled along the track by a linear motor;
   a shoulder yaw joint coupled to the translational carriage, the shoulder yaw joint being actuated by a shoulder yaw motor;
   a shoulder pitch joint coupled to the shoulder yaw joint, the shoulder pitch joint including an arm, a wrist mount coupled to the arm, struts coupled between the wrist mount and the shoulder yaw joint to form a 3D parallelogram, and a shoulder pitch motor coupled to actuate the shoulder pitch joint, the struts, the arm, and the wrist mount;
   a yaw-pitch-roll wrist coupled to the wrist mount, the yaw-pitch-roll wrist including a yaw joint actuated by one or more wrist yaw motors and a differentially driven pitch-roll joint actuated by differentially driven pitch-roll motors; and
   an instrument mount coupled to the yaw-pitch-roll wrist, the instrument mount having one or more instrument motors providing an instrument drive.

2. The manipulator of claim 1, further including a controller, the controller being coupled to the linear motor, the shoulder yaw motor, the shoulder pitch motor, the one or more wrist yaw motors, the differentially driven pitch-roll motors, and the one or more instrument motors, the controller providing signals to position the manipulator and to coordinate insertion of a needle-based instrument attached to the instrument mount.

3. The manipulator of claim 2, wherein the yaw-pitch-roll wrist can be rotated such that the instrument mount is positioned to minimize patient interference.

4. The manipulator of claim 1, wherein the instrument mount couples with an instrument through a sterile adaptor.

5. The manipulator of claim 2, wherein the needle-based instrument is a biopsy instrument.

6. The manipulator of claim 2, wherein the needle-based instrument is an ablation instrument.

7. The manipulator of claim 2, wherein the needle-based instrument includes fiducials for location of a needle of the needle based instrument in an image.

8. The manipulator of claim 2, wherein the controller determines a position of the manipulator based on signals provided to the linear motor, the shoulder yaw motor, the shoulder pitch motor, the one or more wrist yaw motors, the differentially driven pitch-roll motors, and the one or more instrument motors.

9. The manipulator of claim 8, wherein the controller further determines the position of the manipulator based on one or more sensors mounted on the manipulator.

10. The manipulator of claim 1, wherein the translational carriage includes a translational positional sensor, the translational positional sensor determining a position of the translational carriage on the track.

11. The manipulator of claim 10, wherein the translational positional sensor is a resistance sensor.

12. The manipulator of claim 10, wherein the translational positional sensor is an optical sensor and an optical encoder is positioned on the track.

13. The manipulator of claim 1, wherein the translational carriage includes bearings that engage rails on the track.

14. The manipulator of claim 1, wherein the shoulder yaw joint includes:
   a base coupled to the translational carriage and the shoulder yaw motor;
   a support housing coupled to the base;
   a shaft passing through the support housing and the base; and
   a pulley gear coupled to an end of the shaft, the pulley gear engaging the shoulder yaw motor so that the shoulder yaw motor can actuate rotation of the shaft.

15. The manipulator of claim 14, wherein the support housing includes receivers for the struts.

16. The manipulator of claim 14, wherein the shoulder pitch joint is coupled to the shaft.

17. The manipulator of claim 1, wherein the shoulder pitch joint includes:
   a cross support coupled to receive the shoulder yaw joint;
   a first pulley gear attached to the cross support;
   an arm coupled to rotate around the cross support, the shoulder pitch motor being fixed to the arm and driving a second pulley gear, the second pulley gear engaging the first pulley gear such that rotation of the arm on the cross support is actuated by the shoulder pitch motor; and
   a counter balance attached to the arm to counter balance weight applied to the wrist mount.

18. The manipulator of claim 17, wherein the wrist mount includes:
   a wrist mount cross support coupled to the arm to allow rotation of the wrist mount cross support in the arm;
   a shaft attached to the wrist mount cross support; and
   one or more receivers rotatably coupled on the shaft, the one or more receivers receiving the struts.

19. The manipulator of claim 18, further including a shoulder pitch positional sensor coupled between the arm and wrist mount cross support.

20. The manipulator of claim 18, further including a shoulder yaw positional sensor coupled between the shaft and the one or more receivers.

21. The manipulator of claim 1, wherein the yaw-pitch-roll wrist includes:
   a first section attached to the wrist mount of the shoulder pitch joint, the first section including one or more wrist yaw motors; and
   a second section rotatably engaging the first section so that the second section rotates with respect to the first section when actuated by the one or more wrist yaw motors, the second section including a differential gear apparatus that engages the differently driven pitch-roll motors, the differential gear apparatus providing a roll and a pitch when coupled to a mount gear.

22. The manipulator of claim 21, wherein the differential gear apparatus includes:
   a core that receives a mount shaft that is attached to the mount gear and a shaft fixed to the second section such that the core rotates about the shaft fixed to the second section;
   a first wheel with a first gear arranged to rotate around the shaft fixed to the second section, the first gear engaging the mount gear, the first wheel being driven by a first pitch-roll motor; and
   a second wheel with a second gear arranged to rotate around the shaft fixed to the second section, the second gear engaging the mount gear, the second wheel being driven by a second pitch-roll motor.

23. The manipulator of claim 22, wherein a first differential position sensor is coupled between the second section and the first gear, and a second differential position sensor is coupled between the second section and the second gear.

24. The manipulator of claim 1, wherein the instrument mount includes:
   a mount shaft and mount gear that couples to the yaw-pitch-roll wrist; and
   a position sensor coupled between a housing of the instrument mount and the instrument drive.

* * * * *